United States Patent
Kitamura et al.

(10) Patent No.: US 11,553,957 B2
(45) Date of Patent: Jan. 17, 2023

(54) SURGICAL TREATMENT INSTRUMENT

(71) Applicant: OLYMPUS CORPORATION, Hachioji (JP)

(72) Inventors: Ojiro Kitamura, Hachioji (JP); Yusuke Takei, Hino (JP); Yuki Kawaguchi, Koshu (JP)

(73) Assignee: OLYMPUS CORPORATION, Tokyo (JP)

( * ) Notice: Subject to any disclaimer, the term of this patent is extended or adjusted under 35 U.S.C. 154(b) by 957 days.

(21) Appl. No.: 16/376,215

(22) Filed: Apr. 5, 2019

(65) Prior Publication Data

US 2019/0223941 A1    Jul. 25, 2019

Related U.S. Application Data

(63) Continuation of application No. PCT/JP2016/079982, filed on Oct. 7, 2016.

(51) Int. Cl.
| | |
|---|---|
| *A61B 18/14* | (2006.01) |
| *A61B 17/29* | (2006.01) |
| *A61B 18/00* | (2006.01) |
| *A61B 17/00* | (2006.01) |

(52) U.S. Cl.
CPC .......... *A61B 18/1445* (2013.01); *A61B 17/29* (2013.01); *A61B 2017/00367* (2013.01); *A61B 2017/00398* (2013.01); *A61B 2017/00477* (2013.01); *A61B 2017/293* (2013.01); *A61B 2017/2903* (2013.01); *A61B 2017/2905* (2013.01); *A61B 2017/2927* (2013.01);
(Continued)

(58) Field of Classification Search
CPC ...... A61B 18/1445; A61B 2017/00367; A61B 2017/00398; A61B 2017/00477; A61B 2017/2903; A61B 2017/2905
See application file for complete search history.

(56) References Cited

U.S. PATENT DOCUMENTS

| | | |
|---|---|---|
| 2009/0090764 A1 | 4/2009 | Viola |
| 2010/0331879 A1 | 12/2010 | Harris et al. |
| 2012/0074200 A1 | 3/2012 | Schmid et al. |

(Continued)

FOREIGN PATENT DOCUMENTS

| | | |
|---|---|---|
| CN | 103118617 A | 5/2013 |
| JP | 2007-526805 A | 9/2007 |

(Continued)

OTHER PUBLICATIONS

Dec. 27, 2016 International Search Report issued in International Patent Application No. PCT/JP2016/079982.
(Continued)

*Primary Examiner* — Anna K Kinsaul
*Assistant Examiner* — Veronica Martin
(74) *Attorney, Agent, or Firm* — Oliff PLC

(57) ABSTRACT

A surgical treatment instrument includes an elongated member an end effector that is bendable with respect to the elongated member, a bending operator operable to bend the end effector, a rotor rotatable about a rotation axis in response to operation of the bending operator, and a transmitter that transmits a driving force to bend the end effector. The bending operator, the rotor, and the transmitter are rotatable about the longitudinal axis together with the elongated member and the end effector.

8 Claims, 13 Drawing Sheets

(52) U.S. Cl.
CPC ............... *A61B 2017/2929* (2013.01); *A61B 2018/00208* (2013.01)

(56) References Cited

U.S. PATENT DOCUMENTS

| | | | | |
|---|---|---|---|---|
| 2012/0078243 | A1* | 3/2012 | Worrell | A61B 17/07207 606/130 |
| 2012/0130420 | A1* | 5/2012 | Nicholas | A61B 17/068 606/205 |
| 2014/0005705 | A1* | 1/2014 | Weir | A61B 18/08 606/169 |
| 2015/0032150 | A1* | 1/2015 | Ishida | A61B 18/1482 606/205 |
| 2015/0066022 | A1 | 3/2015 | Shelton, IV et al. | |

FOREIGN PATENT DOCUMENTS

| | | | |
|---|---|---|---|
| JP | 2009-112795 | A | 5/2009 |
| JP | 2013-540002 | A | 10/2013 |
| JP | 2013-540003 | A | 10/2013 |

OTHER PUBLICATIONS

Apr. 9, 2019 International Preliminary Report on Patentability issued in International Application No. PCT/JP2016/079982.
Feb. 1, 2021 Office Action issued in Chinese Patent Application No. 201680089900.5.

\* cited by examiner

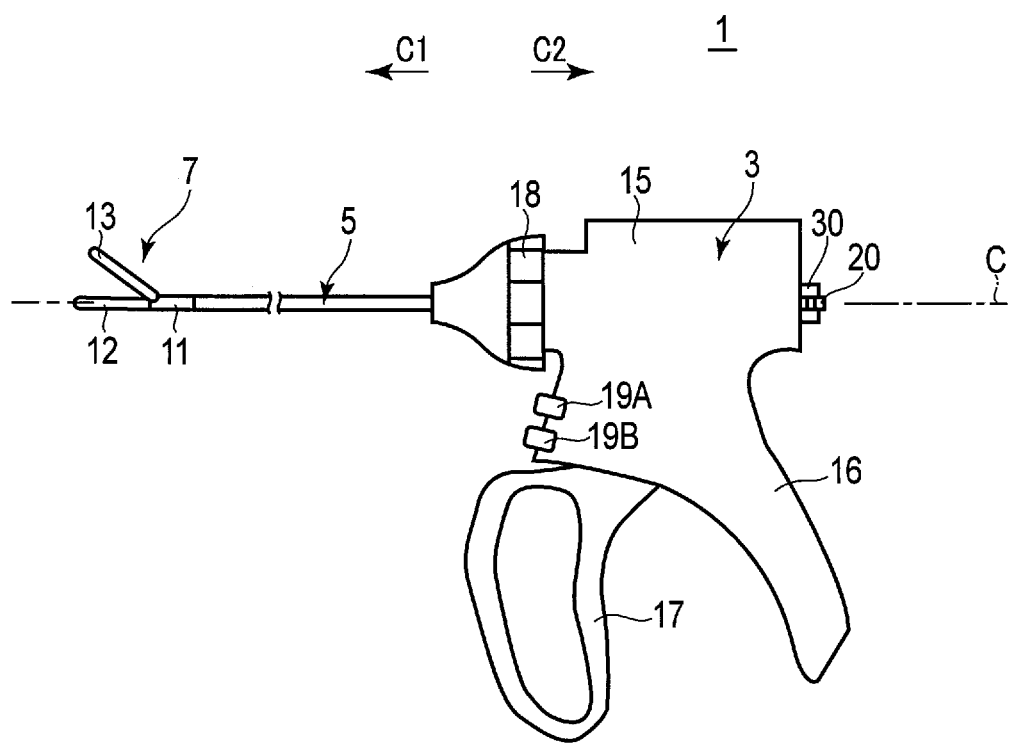
F I G. 1
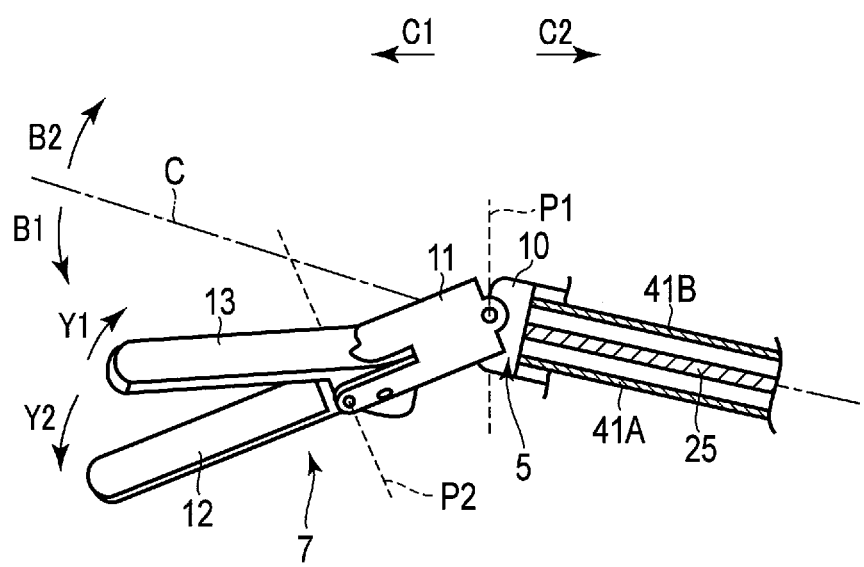
F I G. 2

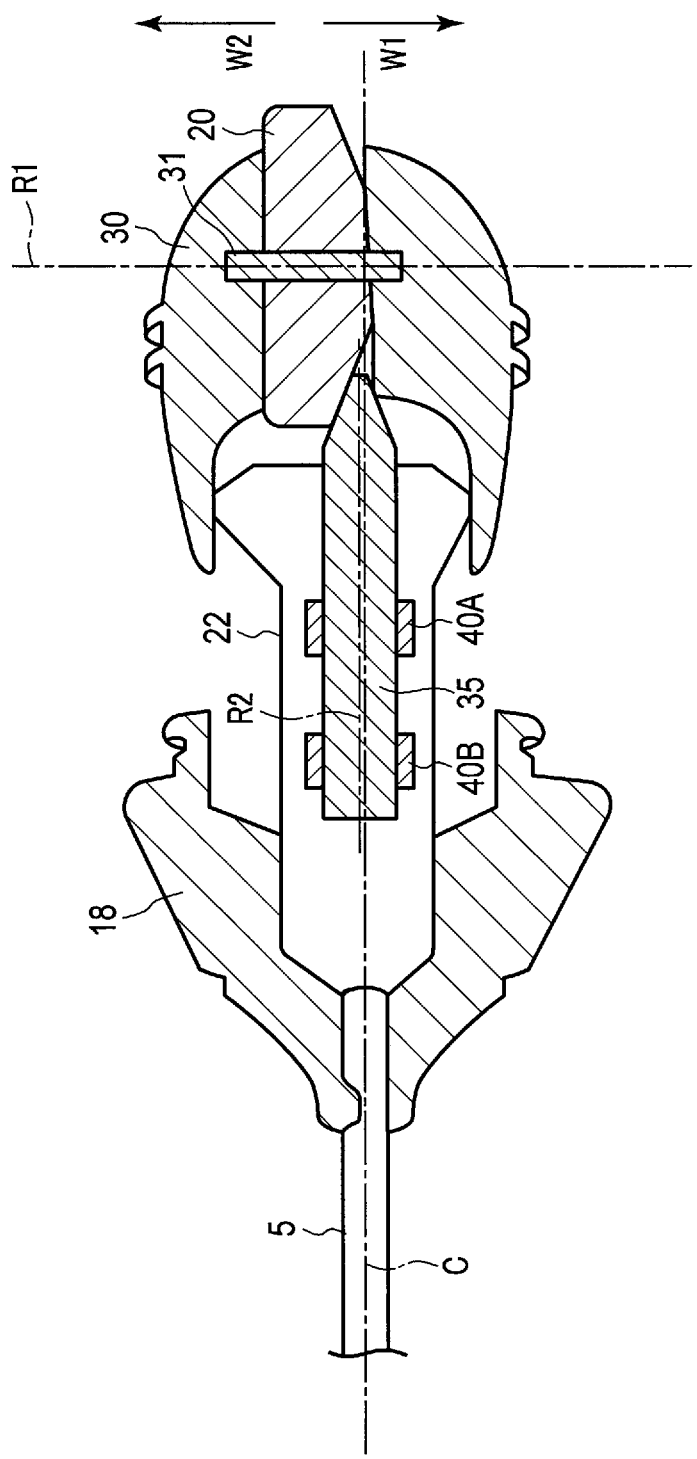
F I G. 4

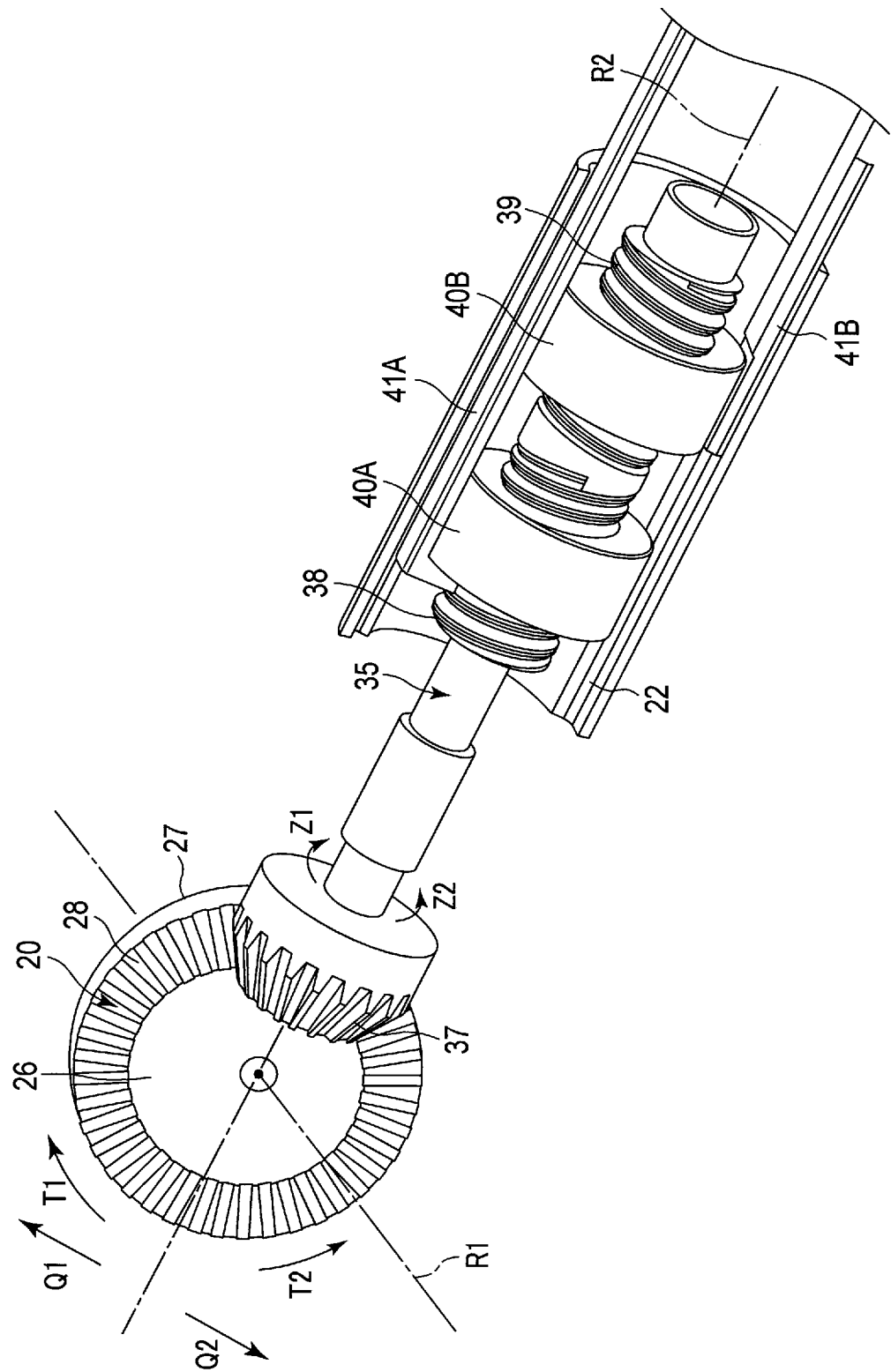
F I G. 5

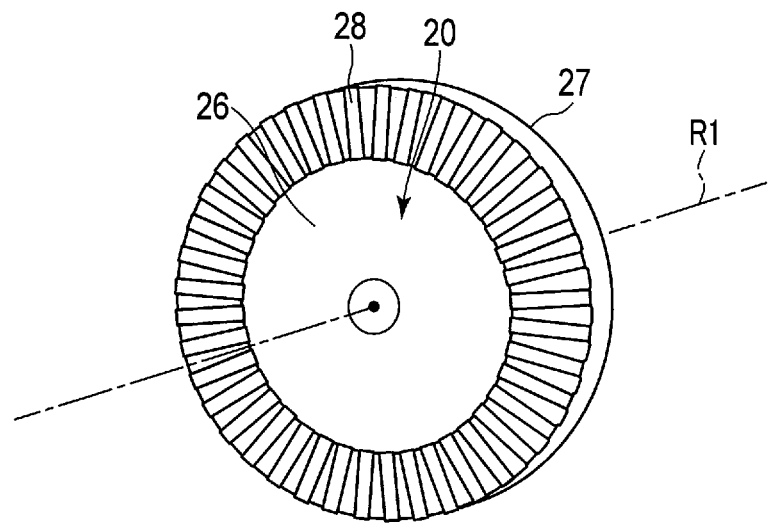
F I G. 6
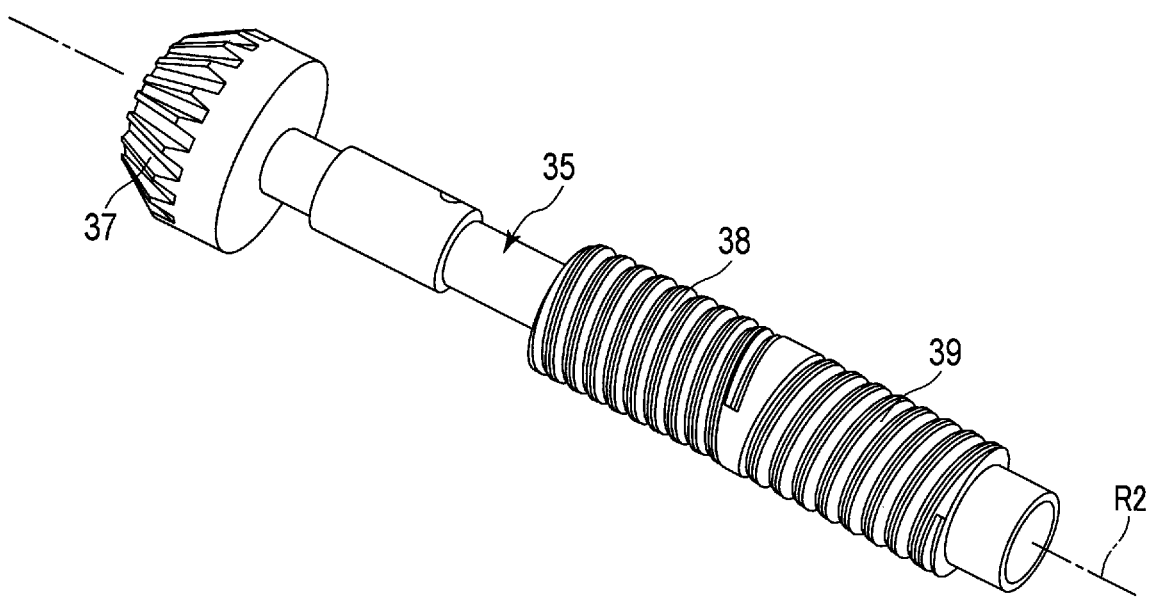
F I G. 7

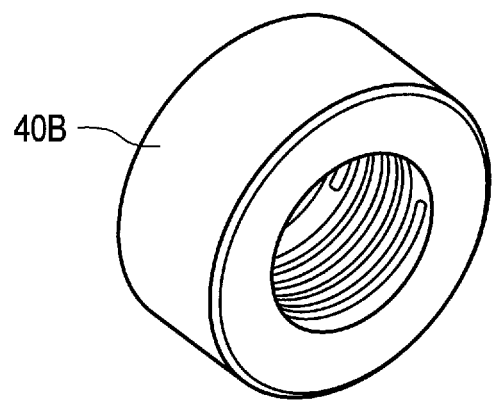
F I G. 8
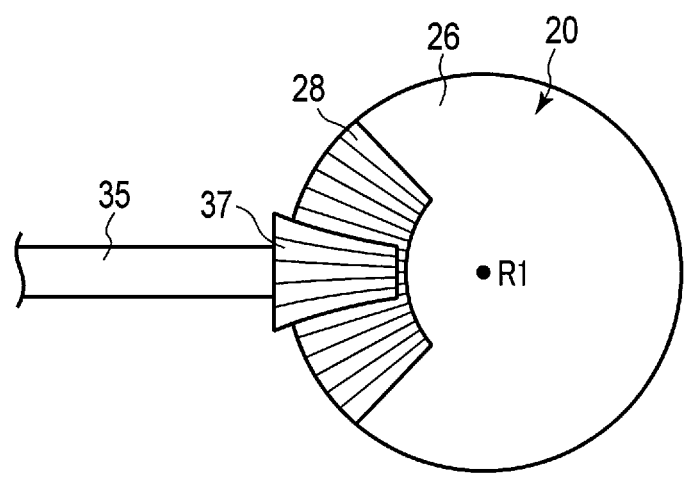
F I G. 9

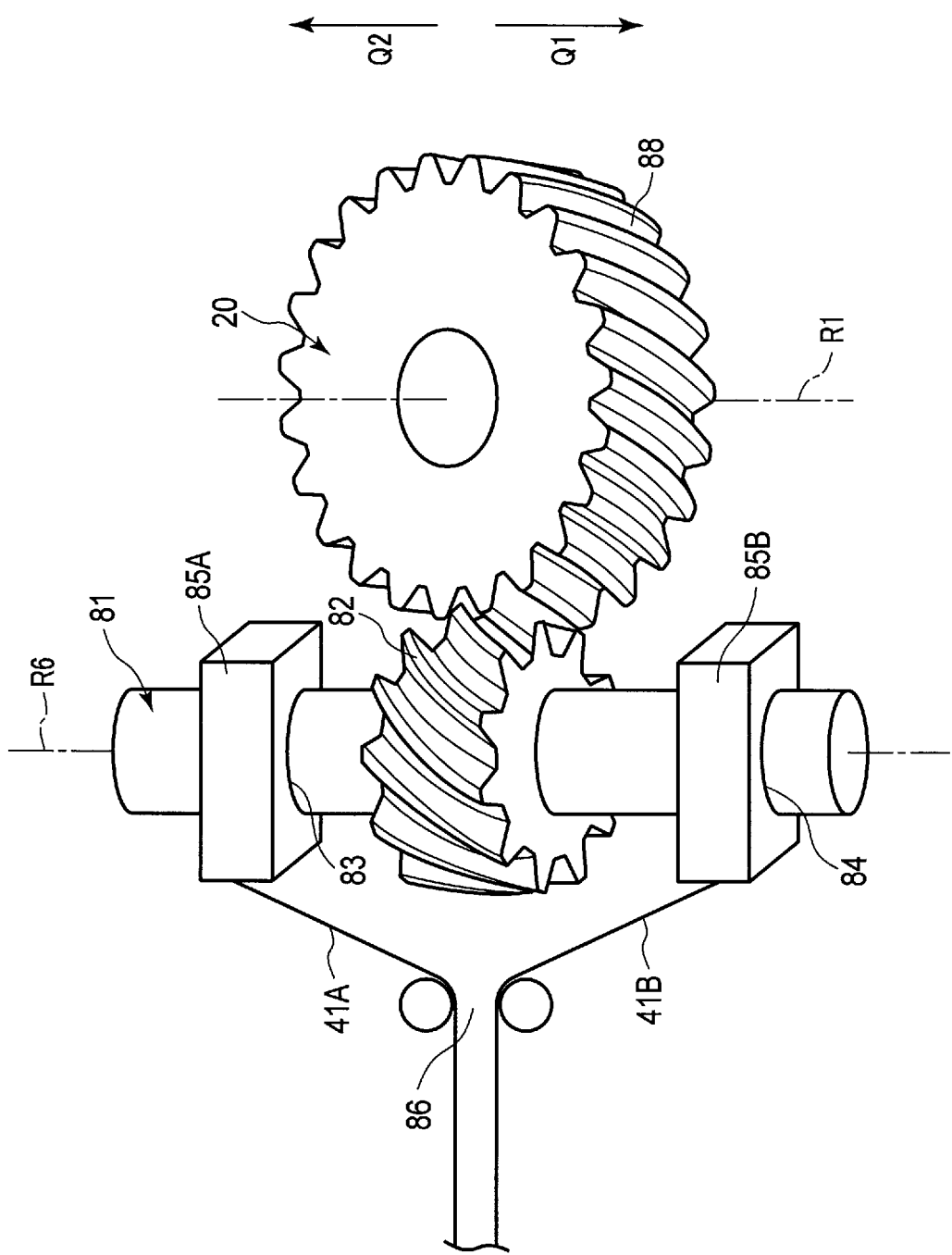
F I G. 17

SURGICAL TREATMENT INSTRUMENT

This is a Continuation Application of PCT Application No. PCT/JP2016/079982, filed Oct. 7, 2016, the entire contents of which are incorporated herein by reference.

BACKGROUND

Exemplary embodiments relate to a surgical treatment instrument in which an end effector for treating a treatment target bends with respect to a shaft.

Surgical instruments including an end effector that is rotatable and bendable can be difficult to use. For example, in U.S. Patent Application Publication No. 2015/0066022, the bending operation dial rotates independently of the rotation operation knob (shaft), so that when the rotation operation knob is rotated about the longitudinal axis, the bending operation dial does not rotate together with the shaft or the end effector. Hence, the relative relationship between the bending direction of the end effector and the operational direction (rotational direction) set by the bending operation dial changes as the angular position of the end effector about the longitudinal axis is changed in response to an operation input performed through the rotation operation knob.

SUMMARY

According to an exemplary embodiment, a surgical treatment instrument includes an elongated member that extends along a longitudinal axis from a proximal side to a distal side, a housing, a distal side of which is connected with the elongated member, an end effector attached to the distal side of the elongated member, and configured to: bend with respect to the elongated member, and rotate together with the elongated member about the longitudinal axis with respect to the housing, a rotation operator configured to be operated to rotate the elongated member and the end effector about the longitudinal axis with respect to the housing, a bending operator attached to the housing, and configured to be operated to bend the end effector with respect to the elongated member, a rotor provided inside the housing and configured to rotate about a rotation axis in response to operation of the bending operator, and a transmitter connected to the rotor and the end effector, and configured to transmit a driving force to the end effector to cause the end effector to bend when the rotor rotates about the rotation axis in response to operation of the bending operator, wherein the bending operator, the rotor, and the transmitter are configured to rotate about the longitudinal axis with respect to the housing together with the elongated member and the end effector in response to operation of the rotation operator.

Advantages will be set forth in the description which follows, and in part will be apparent from the description, or may be learned by practice of exemplary embodiments. The advantages may be realized and obtained by means of the instrumentalities and combinations particularly pointed out hereinafter.

BRIEF DESCRIPTION OF THE DRAWING

The accompanying drawings, which are incorporated in and constitute a part of the specification, illustrate exemplary embodiments.

FIG. 1 is a schematic diagram of a surgical treatment instrument according to an exemplary embodiment.

FIG. 2 is a schematic perspective view of a configuration of an end effector according to an exemplary embodiment.

FIG. 4 is a schematic sectional view of the internal configuration of the housing according to an exemplary embodiment, which is observed at a cross section along the longitudinal axis.

FIG. 5 is a schematic perspective view of the inside of a base member according to an exemplary embodiment.

FIG. 6 is a schematic perspective view of a second operation member according to an exemplary embodiment.

FIG. 7 is a schematic perspective view of a rotor according to an exemplary embodiment.

FIG. 8 is a schematic perspective view of a connecting member according to an exemplary embodiment.

FIG. 9 is a schematic view of the inside of a base member according to an exemplary embodiment, which is observed from one side in a direction along the rotation axis of the second operation member.

FIG. 17 is a schematic perspective view of the inside of a base member according to an exemplary embodiment.

DETAILED DESCRIPTION

Figure 3:
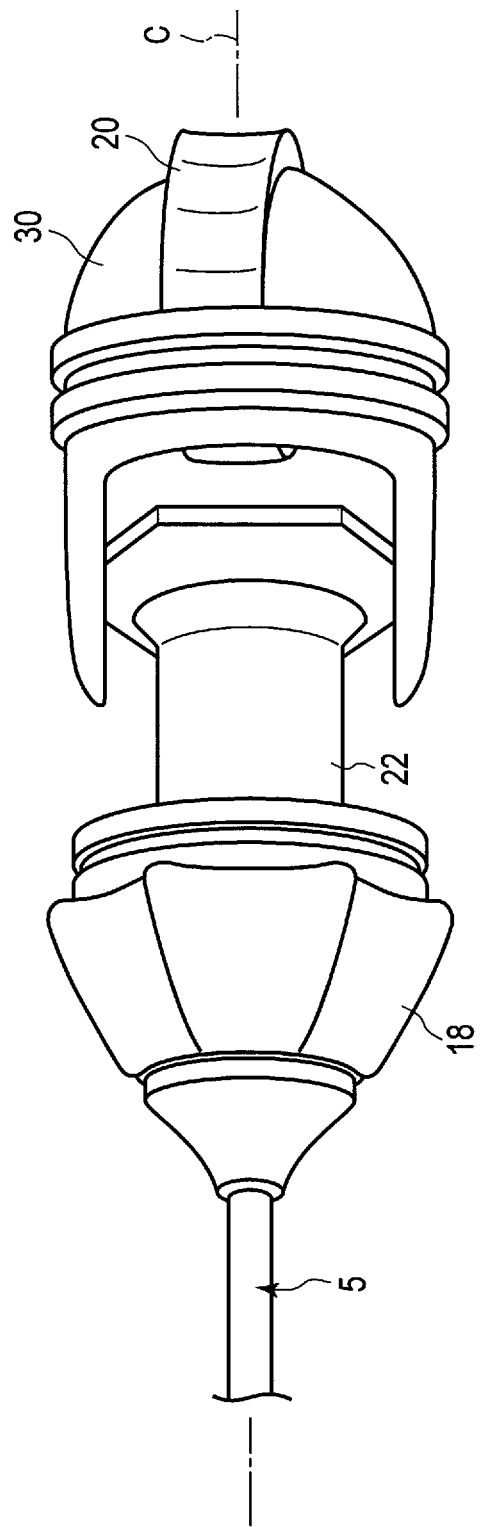
FIG. 3 is a schematic perspective view of an internal configuration of a housing according to an exemplary embodiment.

An exemplary embodiment will be described with reference to FIGS. 1 to 12.

FIG. 1 is a diagram illustrating a configuration of a surgical treatment instrument 1 according to an exemplary embodiment. As illustrated in FIG. 1, the surgical treatment instrument 1 includes a holdable housing 3 and a tubular shaft 5 connected to the housing 3. The shaft 5 defines a longitudinal axis C. The direction along the longitudinal axis C is defined as a longitudinal direction. One side in the longitudinal direction is defined as the distal side (arrow C1 side in FIG. 1), and the opposite side from the distal side is defined as the proximal side (arrow C2 side in FIG. 1). The shaft 5 extends from the proximal side to the distal side along the longitudinal axis C, and is connected to the distal side of the housing 3.

The shaft 5 has a central axis substantially coaxial with the longitudinal axis C, and is installed to be rotatable about the longitudinal axis C with respect to the housing 3. A rotation operation knob 18 as a first operation member (a rotation operator) is attached to the proximal end of the shaft 5. The proximal end of the shaft 5 is inserted from the distal side into the rotation operation knob 18 and fixed to the rotation operation knob (rotation operation input unit) 18. The shaft 5 is extended from the rotation operation knob 18 toward the distal side. An end effector 7 for treating a treatment target is attached to the distal side of the shaft 5. When the rotation operation knob 18 is rotated about the longitudinal axis C with respect to the housing 3, the operation of rotating the end effector 7 about the longitudinal axis C is input through the rotation operation knob 18. When an operation input is performed through the rotation operation knob 18, a driving force (rotational driving force) is transmitted to the shaft 5, causing the rotation operation knob 18 and the shaft 5 to rotate together about the longitudinal axis C with respect to the housing 3. Although the rotation operator is illustrated as a knob 18, it may have any suitable structure for being operable to rotate the shaft and the end effector about the longitudinal axis. For example, the rotation operator may be a knob, a dial, a lever, or a switch.

FIG. 2 is a diagram illustrating a configuration of the end effector 7. As illustrated in FIG. 2, the end effector 7 includes an effector base 11 attached to the shaft 5, a first grasping piece 12 fixed to the effector base 11, and a second grasping piece 13 pivotably connected to the effector base 11. The effector base 11 is attached to the shaft 5 such that the effector base 11 is pivotable about a pivot axis (bending pivot axis) P1 with respect to the shaft 5. The pivot axis P1 extends along a direction intersecting with (substantially perpendicular to) the longitudinal direction of the shaft 5. As the end effector 7 including the effector base 11 pivots about the pivot axis P1 with respect to the shaft 5, the end effector 7 bends with respect to the shaft 5 in the directions indicated by arrow B1 and arrow B2 in FIG. 2.

The second grasping piece 13 can be pivoted about a pivot axis (opening/closing pivot axis) P2 with respect to the effector base 11. The pivot axis P2 extends along a direction intersecting with (substantially perpendicular to) the longitudinal direction and also intersecting with (substantially perpendicular to) the direction in which the pivot axis P1 extends. When the second grasping piece 13 pivots about the pivot axis P2, the first grasping piece 12 and the second grasping piece 13 are opened or closed with respect to each other in the end effector 7. More specifically, when the second grasping piece 13 pivots, the end effector 7 opens or closes in the directions indicated by arrow Y1 and arrow Y2 in FIG. 2. Both the first grasping piece 12 and the second grasping piece 13 may be attached to be pivotable with respect to the effector base 11 (e.g., about the pivot axis P2). In this case, the first grasping piece 12 and the second grasping piece 13 are opened or closed with respect to each other by pivoting the first grasping piece 12 and the second grasping piece 13 so as to open or close the end effector 7. In the present embodiment, a treatment target, such as a body tissue, is grasped between the first grasping piece 12 and the second grasping piece 13 in order to treat the treatment target.

As illustrated in FIG. 1, the housing 3 includes a housing main body 15, which is extended along the longitudinal axis C, and a grip (fixed handle) 16, which is extended from the housing main body 15 in a direction away from the longitudinal axis C. The shaft 5 is connected to the housing main body 15 from the distal side. A handle (movable handle) 17 is pivotably attached to the housing 3. The handle 17 is positioned on the side where the grip 16 is positioned with respect to the longitudinal axis C, and positioned on the distal side with respect to the grip 16 in the present embodiment. As the handle 17 pivots with respect to the housing 3, and opens or closes with respect to the grip 16, the operation for opening or closing the end effector 7 as described above is input through the handle 17, which is an opening/closing operation input unit. The handle 17 and the second grasping piece 13 are connected to each other via a movable member 25 extending in the shaft 5 along the longitudinal axis C. By opening or closing the handle 17, which is an opening/closing operation input unit, with respect to the grip 16, the movable member 25 moves along the longitudinal axis C with respect to the shaft 5 and the housing 3, and the second grasping piece 13 pivots about the pivot axis P2. As a result, the pair of grasping pieces 12 and 13 open or close.

Operation buttons 19A and 19B, which are energy operation input units, are attached to the housing 3. Performing an operation input through the operation button 19A, for example, supplies a high-frequency electric energy to the grasping pieces 12 and 13. Then, a high-frequency current is applied to the treatment target held between the grasping pieces 12 and 13 to thereby treat the treatment target. Performing an operation input through the operation button 19B supplies electric energy to, for example, a heating element (not illustrated) provided to the end effector 7. Then, the heat generated by the heating element is used to treat the treatment target. The energy supplied to the end effector 7 is not limited to the foregoing energy. Other types of energy used for treatment may be supplied to the end effector 7 by performing an operation input through the operation buttons 19A and 19B.

FIGS. 3 and 4 are diagrams illustrating the internal configuration of the housing 3 and the internal configuration of the rotation operation knob 18. FIG. 3 is a perspective view, and FIG. 4 illustrates a cross section that is substantially parallel to the longitudinal axis C. In the housing 3 (the housing main body 15), a tubular rotation base 22 as a base member (a base) is attached to the shaft 5 (the rotation operation knob 18) from the proximal side, as illustrated in FIGS. 3 and 4. The rotation of the rotation base 22 about the longitudinal axis C with respect to the shaft 5 is restricted. For example, in a connecting portion between the rotation base 22 and the rotation operation knob 18, the cross-sectional shape of the outer peripheral surface of the rotation base 22 and the cross-sectional shape of the inner peripheral surface of the rotation operation knob 18 that are perpendicular to the longitudinal axis C are designed to be a polygonal shape, a D shape, or the like, so that the rotation of the rotation base 22 and the shaft 5 with respect to each other about the longitudinal axis C is restricted. The rotation base 22 is extended along the longitudinal axis C.

When the rotation operation knob 18 rotates about the longitudinal axis C in response to the operation input performed through the rotation operation knob 18, a driving force (rotational driving force) is transmitted to the rotation base 22 attached to the rotation operation knob 18, causing the rotation base 22 to rotate, with respect to the housing 3, about the longitudinal axis C together with the shaft 5 attached to the rotation operation knob 18. Since the shaft 5 is fixed to the rotation operation knob 18, the driving force (rotational driving force) is transmitted to the rotation base 22 through the rotation operation knob 18 when the shaft 5 is rotated.

According to the present embodiment, the movable member 25 is rotatable about the longitudinal axis C together with the shaft 5. Hence, in response to the operation input performed through the rotation operation knob 18, the end effector 7 rotates about the longitudinal axis C with respect to the housing 3 together with the shaft 5 and the movable member 25. As the end effector 7 rotates about the longitudinal axis C, the angular position of the end effector 7 about the longitudinal axis C with respect to the housing 3 changes.

As the end effector 7 rotates, the pivot axes P1 and P2 also rotate about the longitudinal axis C with respect to the housing 3, and the extending directions of the pivot axes P1 and P2 change accordingly. Thus, the bending directions of the bending movement of the end effector 7 (the side indicated by arrow B1 and the side indicated by arrow B2 in FIG. 2) and the opening/closing directions of the opening/closing movement thereof (the side indicated by arrow Y1 and the side indicated by arrow Y2 in FIG. 2) also change. However, the bending directions of the end effector 7 intersect with (are substantially perpendicular to) the longitudinal direction; and the opening/closing directions of the end effector 7 intersect with (are substantially perpendicular to) the longitudinal direction and also intersect with (are substantially perpendicular to) the bending directions of the bending movement, regardless of the angular position of the end effector 7 about the longitudinal axis C.

Inside the housing 3 (the housing main body 15), a rotation base 30 as a base member (a base) is attached to the rotation base 22 from the proximal side. The rotation base 30 is positioned closer to the proximal side than the rotation base 22. The rotation of the rotation base 30 about the longitudinal axis C with respect to the rotation base 22 is restricted. For example, in a connecting portion between the rotation bases 22 and 30, the cross-sectional shape of the outer peripheral surface of the rotation base 22 and the cross-sectional shape of the inner peripheral surface of the rotation base 30 that are perpendicular to the longitudinal axis C are designed to be a polygonal shape, a D shape, or the like, so that the rotation of the rotation bases 22 and 30 with respect to each other about the longitudinal axis C is restricted.

A bending operation dial 20 as a second operation member (a bending operator) is attached to the housing 3. In the present embodiment, the bending operation dial (bending operation input unit) 20 is positioned on the proximal side apart from the rotation operation knob 18. An operation for bending the end effector 7 as described above is input through the bending operation dial 20. The bending operation dial 20 is attached to the housing 3 via the rotation base 30. The rotation base 30 and the bending operation dial 20 are rotatable about the longitudinal axis C with respect to the housing 3. Although the bending operator is illustrated as a dial 20, it may have any suitable structure for being operable to bend the end effector with respect to the shaft. For example, the bending operator may be a knob, a dial, a lever, or a switch.

FIG. 5 is a perspective view illustrating the internal configuration of the rotation bases 22 and 30. FIG. 6 is a view of the bending operation dial 20. As illustrated in FIGS. 4 to 6, the bending operation dial 20 is attached to the rotation base 30 via a support shaft 31. The bending operation dial 20 is rotatable about a central axis R1, which is the central axis of the support shaft 31, with respect to the rotation base 30. That is, the central axis R1 is the central axis (rotation axis) of the bending operation dial. The bending operation dial 20 is rotated about the central axis R1 so that an operation for bending the end effector 7 is input. At this time, the directions indicated by arrow Q1 and arrow Q2 in FIG. 5 are the operational directions set by the bending operation dial 20. The central axis R1 is extended along the direction intersecting with (substantially perpendicular to) the longitudinal axis C, and along the direction intersecting with (substantially perpendicular to) the operational directions set by the bending operation dial 20.

One side along the central axis R1 is defined as a first width direction side (arrow W1 side in FIG. 4) of the bending operation dial 20, and the opposite side from the first width direction side is defined as a second width direction side (arrow W2 side in FIG. 4). The bending operation dial 20 includes a first side surface 26 facing the first width direction side and a second side surface 27 facing the second width direction side. A gear section 28 is formed over the whole circumference of the first side surface 26 around the central axis R1. In the present embodiment, a part of the gear section 28 is exposed to the outside of the housing 3.

A shaft 35 as a rotor is provided inside the rotation base 22. FIG. 7 is a view of the shaft 35. As illustrated in FIGS. 5 and 7, the shaft 35 has a central axis (rotation axis) R2. In the present embodiment, the central axis R2 extends substantially in parallel with the longitudinal axis C. In one embodiment, the central axis R2 is substantially coincident with the longitudinal axis C (coaxial). The shaft 35 extends along the central axis R2.

The shaft 35 is attached to the rotation base 22 in a state where the movement of the shaft 35 along the central axis R2 with respect to the rotation base 22 is restricted. The shaft 35 is rotatable about the central axis R2 with respect to the rotation base 22.

A gear section 37 is formed over the whole circumference of the proximal end of the shaft 35 around the central axis R2. The gear section 37 meshes with the gear section 28 of the bending operation dial 20. When the bending operation dial 20 rotates about the central axis R1 in response to an operation input performed through the bending operation dial 20, a driving force (rotational driving force) is transmitted to the gear section 37 through the gear section 28, causing the shaft 35 to rotate about the central axis R2. In the present embodiment, a bevel gear is used for the gear section 28 and the gear section 37; however, the gear section 28 and the gear section 37 are not limited thereto. For example, a crown gear may be used for the gear section 28, and a spur gear may be used for the gear section 37.

The shaft 35 includes a right-hand screw portion (first screw portion) 38 and a left-hand screw portion (second screw portion) 39. The right-hand screw portion 38 (first screw) includes a right-hand thread formed around the central axis R2. The left-hand screw portion (second screw) 39 includes a left-hand thread formed around the central axis R2. Therefore, the winding direction of the left-hand screw portion 39 is opposite to that of the right-hand screw portion 38, so that the left-hand screw portion 39 includes a thread reversed with respect to the right-hand screw portion 38.

A nut 40A as a first connecting member (a first connecter) is screwed to the right-hand screw portion 38. A nut 40B as a second connecting member (a second connecter) is screwed to the left-hand screw portion 39. FIG. 8 is a view of the nut 40B. An internal thread of the right-hand thread is formed on the inner peripheral surface of the nut 40A. An internal thread of the left-hand thread is formed on the inner peripheral surface of the nut 40B. The nuts 40A and 40B are attached to the rotation base 22. The rotation of the nuts 40A and 40B about the central axis R2 with respect to the rotation base 22 is restricted. The nuts 40A and 40B are movable along the central axis R2 with respect to the rotation base 22.

When the shaft 35 rotates about the central axis R2 in response to the operation input performed through the bending operation dial 20, the right-hand screw portion 38 rotates about the central axis R2 with respect to the nut 40A, and the left-hand screw portion 39 rotates about the central axis R2 with respect to the nut 40B. As a result, the nuts 40A and 40B move along the central axis R2 with respect to the shaft 35. That is, the shaft 35 as a rotor converts the rotational motion about the central axis R2 generated by the operation input performed through the bending operation dial 20 into a rectilinear motion of the nuts 40A and 40B along the central axis R2. The winding direction of the left-hand screw portion 39 is opposite to that of the right-hand screw portion 38. Therefore, the nuts 40A and 40B move in directions opposite to each other along the central axis R2.

The proximal end (one end) of a bending wire 41A as a transmission member (a transmitter) is connected to the nut 40A. The bending wire (bending drive member) 41A is extended along the longitudinal axis C, and is extended through the inside of the rotation base 22 and the inside of the shaft 5 toward the distal side. Also, the proximal end (one end) of a bending wire 41B as a transmission member (a transmitter) is connected to the nut 40B. The bending wire (bending drive member) 41B is extended along the longitudinal axis C and is extended through the inside of the rotation base 22 and the inside of the shaft 5 toward the distal side.

As illustrated in FIG. 2, the distal ends (the other ends) of the bending wires 41A and 41B are connected to the effector base 11 of the end effector 7. When the shaft 35 rotates about the central axis R2 in response to the operation input performed through the bending operation dial 20, the nuts 40A and 40B move in directions opposite to each other with respect to the rotation base 22 along the central axis R2. Thus, the bending wires 41A and 41B as transmission members (transmitters) are driven, and the bending wires 41A and 41B move along the longitudinal axis C with respect to the shaft 5. As the bending wires 41A and 41B move, the end effector 7 bends with respect to the shaft 5, as described above. That is, the bending wires 41A and 41B as transmission members (transmitters) transmit the driving force for bending the end effector 7 to the end effector 7.

For example, if the bending operation dial 20 is rotated toward one side of the rotational direction (the side indicated by arrow T1 in FIG. 5) by the operation input for moving the bending operation dial 20 toward one side of the operational direction (the side indicated by arrow Q1 in FIG. 5), then the shaft 35 rotates toward one side of the rotational direction (the side indicated by arrow Z1 in FIG. 5). Thus, the nut 40A moves toward the distal side with respect to the shaft 35 and the rotation base 22, and the nut 40B moves toward the proximal side with respect to the shaft 35 and the rotation base 22. Accordingly, the nut 40A and the nut 40B move in directions opposite to each other. The bending wire 41A connected to the nut 40A moves toward the distal side (to be loosened), and the bending wire 41B connected to the nut 40B moves toward the proximal side (to be tightened), causing the end effector 7 to bend toward one side of the bending direction (the side indicated by arrow B2 in FIG. 2) with respect to the shaft 5 (the longitudinal axis C).

On the other hand, if the bending operation dial 20 is rotated toward the other side of the rotation direction (the side indicated by arrow T2 in FIG. 5) by the operation input for moving the bending operation dial 20 toward the other side of the operational direction (the side indicated by arrow Q2 in FIG. 5), then the shaft 35 rotates toward the other side of the rotational direction (the side indicated by arrow Z2 in FIG. 5). Thus, the nut 40A moves toward the proximal side with respect to the shaft 35 and the rotation base 22, and the nut 40B moves toward the distal side with respect to the shaft 35 and the rotation base 22. Accordingly, the nut 40A and the nut 40B move opposite to each other. The bending wire 41A moves toward the proximal side, and the bending wire 41B moves toward the distal side, causing the end effector 7 to bend toward the other side of the bending direction (the side indicated by arrow B1 in FIG. 2) with respect to the shaft 5 (the longitudinal axis C).

The bending wire 41B may be connected to the nut 40A, and the bending wire 41A may be connected to the nut 40B. In this case, when the operation input for moving the bending operation dial 20 toward one side of the operational direction (the side indicated by arrow Q1 in FIG. 5) is performed, for example, the bending wire 41B connected to the nut 40A moves toward the distal side (to be loosened), and the bending wire 41A connected to the nut 40B moves toward the proximal side (to be tightened), causing the end effector 7 to bend toward one side of the bending direction (the side indicated by arrow B1 in FIG. 2) with respect to the shaft 5 (the longitudinal axis C). Also, in response to the operation input for moving the bending operation dial 20 toward the other side of the operational direction (the side indicated by arrow Q2 in FIG. 5), the bending wire 41B connected to the nut 40A moves toward the proximal side (to be tightened), and the bending wire 41A connected to the nut 40B moves toward the distal side (to be loosened), causing the end effector 7 to bend toward the other side of the bending direction (the side indicated by arrow B2 in FIG. 2) with respect to the shaft 5 (the longitudinal axis C).

Inside the housing 3 (the housing main body 15), the rotation base 30 is connected to the rotation base 22 from the proximal side. The rotation of the rotation base 22 and the rotation base 30 about the longitudinal axis C with respect to each other is restricted. Therefore, the rotation bases 22 and 30, which connect the shaft 5 and the bending operation dial 20, are rotatable about the longitudinal axis C together with the shaft 5 and the bending operation dial 20.

With the foregoing configuration, the end effector 7, the shaft 5, and the rotation base 22 rotate about the longitudinal axis C in response to the operation input performed through the rotation operation knob (first operation member) 18, thereby transmitting a driving force (rotational driving force) to the rotation base 30 from the shaft 5 through the rotation base 22. This causes the rotation bases 22 and 30 to rotate, together with the end effector 7 and the shaft 5, about the longitudinal axis C with respect to the housing 3. At this time, the driving force (rotational driving force) is also transmitted from the rotation base 22 to the shaft 35 and the nuts 40A and 40B, which are attached to the rotation base 22, so that the shaft 35 and the nuts 40A and 40B rotate, together with the rotation base 22, about the longitudinal axis C with respect to the housing 3. The driving force (rotational driving force) is also transmitted from the rotation base 30 to the bending operation dial 20 and the support shaft 31, which are attached to the rotation base 30, so that the bending operation dial 20 and the support shaft 31 rotate, together with the rotation base 30, with respect to the housing 3 about the longitudinal axis C. Namely, according to the present embodiment, when the shaft 5 rotates about the longitudinal axis C with respect to the housing 3 in response to the operation input performed through the rotation operation knob 18, which is the first operation member (a rotation operator), the bending operation dial 20, which is the second operation member (a bending operator), and the end effector 7 also rotate about the longitudinal axis C together with the shaft 5 with respect to the housing 3. Further, when the end effector 7 and the shaft 35 rotate with respect to the housing 3 about the longitudinal axis C in response to the operation input performed through the rotation operation knob 18, the bending wires 41A and 41B connecting the end effector 7 and the shaft 35 also rotate about the longitudinal axis C.

As the shaft 35 and the bending operation dial 20 rotate, the central axes R1 and R2 also rotate about the longitudinal axis C with respect to the housing 3. At this time, the extending direction of the central axis R1 also changes. This in turn changes the rotational directions of the bending operation dial 20 (the side indicated by arrow T1 and the side indicated by arrow T2 in FIG. 5), thus changing the operational directions of the operation input performed through the bending operation dial 20 (the side indicated by arrow Q1 and the side indicated by arrow Q2 in FIG. 5). However, the operational direction set by the bending operation dial 20 intersects with (is substantially perpendicular to) the longitudinal axis C and the central axis R2, and intersects with (is substantially perpendicular to) the extending direction of the central axis R1, regardless of the angular positions of the rotation base 30 and the bending operation dial 20 about the longitudinal axis C.

As described above, according to the present embodiment, the shaft 5, the end effector 7, and the bending operation dial 20 rotate together about the longitudinal axis C in response to the operation input performed through the rotation operation knob 18. Hence, if the angular position of the end effector 7 about the longitudinal axis C changes due to the rotation of the end effector 7, the angular position of the bending operation dial 20 about the longitudinal axis C changes according to the change in the angular position of the end effector 7. Therefore, when the operation input is performed through the rotation operation knob 18, the operational directions set by the bending operation dial 20 (the side indicated by arrow Q1 and the side indicated by arrow Q2 in FIG. 5) change according to the changes in the bending directions of the end effector 7 (the side indicated by arrow B1 and the side indicated by arrow B2 in FIG. 2). For example, in one embodiment, the end effector 7 is rotated about the longitudinal axis C by the operation input performed through the rotation operation knob 18, from a state in which the bending direction of the end effector 7 and the operational direction set by the bending operation dial 20 are substantially parallel. At this time, the bending operation dial 20 also rotates about the longitudinal axis C together with the end effector 7, so that the state in which the bending direction of the end effector 7 and the operational direction set by the bending operation dial 20 are substantially parallel is maintained even when the angular position of the end effector 7 about the longitudinal axis C changes. Namely, according to the present embodiment, even when the operation input is performed through the rotation operation knob 18, the end effector 7 and the bending operation dial 20 rotate together about the longitudinal axis C without changing the relative relationship between the bending direction of the end effector 7 and the operational direction set by the bending operation dial 20. Also, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

A description will now be given of the operation and effect of the surgical treatment instrument 1 according to the present embodiment. When performing a treatment by using the surgical treatment instrument 1, the end effector 7 is inserted into a body cavity, such as an abdominal cavity. Then, the end effector 7 is brought to a treatment target. At this time, the end effector 7 is rotated about the longitudinal axis C by the operation input performed through the rotation operation knob 18, or the end effector 7 is bent with respect to the shaft 5 by the operation input performed through the bending operation dial 20, so that the end effector 7 is placed at a position that allows the treatment target to be easily gripped. Then, the treatment target is positioned between the pair of the grasping pieces 12 and 13, and the end effector 7 is closed by the operation input performed through the handle 17. Thus, the treatment target is held between the grasping pieces 12 and 13. In this state, an operation input is performed through the operation button 19A or 19B to supply energy to the end effector 7, so that the treatment target is treated using the energy (treatment energy).

According to the present embodiment, the shaft 5, the end effector 7, and the bending operation dial 20 rotate together about the longitudinal axis C in response to the operation input performed through the rotation operation knob 18. Hence, even when the angular position of the end effector 7 about the longitudinal axis C with respect to the housing 3 changes, the relative angular position of the bending operation dial 20 about the longitudinal axis C with respect to the shaft 5 and the end effector 7 remains unchanged. Namely, even when an operation input is performed through the rotation operation knob 18, the end effector 7 and the bending operation dial 20 rotate together about the longitudinal axis C without changing the relative relationship between the bending directions of the end effector 7 (the side indicated by arrow B1 and the side indicated by arrow B2 in FIG. 2) and the operational directions set by the bending operation dial 20 (the side indicated by arrow Q1 and the side indicated by arrow Q2 in FIG. 5). This enables the operator to easily know the bending direction of the end effector 7 regardless of the angular position of the end effector 7 about the longitudinal axis C.

As described above, the present embodiment can provide the surgical treatment instrument 1 that ensures ease of operation for bending the end effector 7 with respect to the shaft 5 regardless of the angular position of the end effector 7 about the longitudinal axis C.

Figure 10:
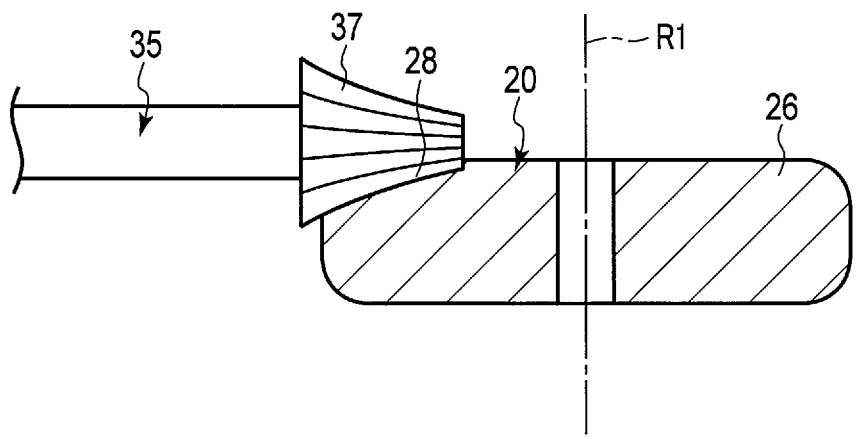
FIG. 10 is a schematic sectional view of the inside of the base member according to an exemplary embodiment, which is observed at a cross section along the longitudinal axis and the rotation axis of the second operation member.

FIGS. 9 and 10 are diagrams illustrating the configuration of the bending operation dial 20 according to another exemplary embodiment. FIG. 9 is a view from the first width direction side, and FIG. 10 illustrates the bending operation dial 20, which is observed at a cross section along the longitudinal axis C and the central axis R1. In this embodiment, the gear section 28 is provided to only a part of the first side surface 26 of the bending operation dial 20 about the central axis R1, as illustrated in FIGS. 9 and 10. The gear section 28 is provided, about the central axis R1, in an area other than the portion where the bending operation dial 20 is exposed to the outside from the housing 3.

In this embodiment, the gear section 28 is not provided in the portion where the bending operation dial 20 is exposed to the outside from the housing 3. Therefore, the gear section 28 is not formed in the portion where the operation input through the bending operation dial 20 is performed by the operator. This enables the operator to safely perform the operation input through the bending operation dial 20 by operating the portion of the bending operation dial 20 where the gear section 28 is not formed.

Figure 11:
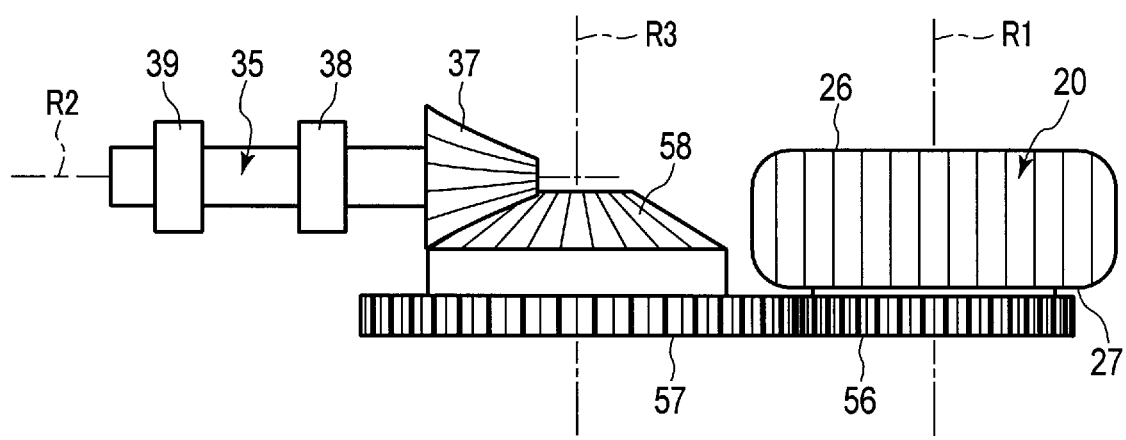
FIG. 11 is a schematic view of the inside of a base member according to an exemplary embodiment.

FIG. 11 is a diagram illustrating the internal configuration of the rotation bases 22 and 30 according to an exemplary embodiment. In this embodiment, the gear section (28) is not provided on the first side surface 26 of the bending operation dial 20, as illustrated in FIG. 11. A spur gear 56 is attached to the second side surface 27. As the bending operation dial 20 rotates with respect to the rotation base 30 about the central axis R1 in response to the operation input performed through the bending operation dial 20, the spur gear 56 rotates together with the bending operation dial 20 about the central axis R1 with respect to the rotation base 30. The spur gear 56 is attached to the bending operation dial 20 inside the housing 3.

A spur gear 57 meshing with the spur gear 56 is provided on the distal side of the spur gear 56. For example, the spur gear 57 is mounted inside the rotation base 22. The spur gear 57 has a central axis (rotation axis) R3. The central axis R3 extends substantially in parallel with the central axis R1. The spur gear 57 is rotatable about the central axis R3 with respect to the rotation base 22. The movement of the spur gear 57 with respect to the rotation base 22 is restricted except the rotation about the central axis R3. The spur gear 56 rotates about the central axis R1 in response to the operation input performed through the bending operation dial 20, whereby the driving force is transmitted to the spur gear 57 via the spur gear 56. Then, the spur gear 57 rotates with respect to the rotation base 22 about the central axis R3.

A gear section 58 is attached to the spur gear 57. The gear section 58 meshes with the gear section 37 of the shaft 35. The gear section 58 rotates together with the spur gear 57 about the central axis R3 with respect to the rotation base 22. The gear section 58 and the spur gear 57 rotate about the central axis R3 in response to the operation input performed through the bending operation dial 20, whereby the driving force is transmitted to the gear section 37 via the gear section 58. Then, the gear section 37 and the shaft 35 rotate with respect to the rotation base 22 about the central axis (rotation axis) R2.

The end effector 7, the shaft 5, the rotation bases 22 and 30, and the bending operation dial 20 together rotate with respect to the housing 3 about the longitudinal axis C in response to the operation input performed through the rotation operation knob 18. At this time, the driving force (rotational driving force) is also transmitted from the rotation base 22 to the shaft 35, the nuts 40A and 40B, the spur gears 56 and 57, and the gear section 58 attached to the rotation base 22 or 30, so that the shaft 35, the nuts 40A and 40B, the spur gears 56 and 57, and the gear section 58 rotate with respect to the housing 3 about the longitudinal axis C together with the rotation base 22. Therefore, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

In this embodiment, the spur gear 56 is mounted inside the housing 3. Therefore, the gear section (28) is not formed in the portion of the bending operation dial 20 that is exposed to the outside from the housing 3. This enables the operator to safely perform the operation input through the bending operation dial 20.

Figure 12:
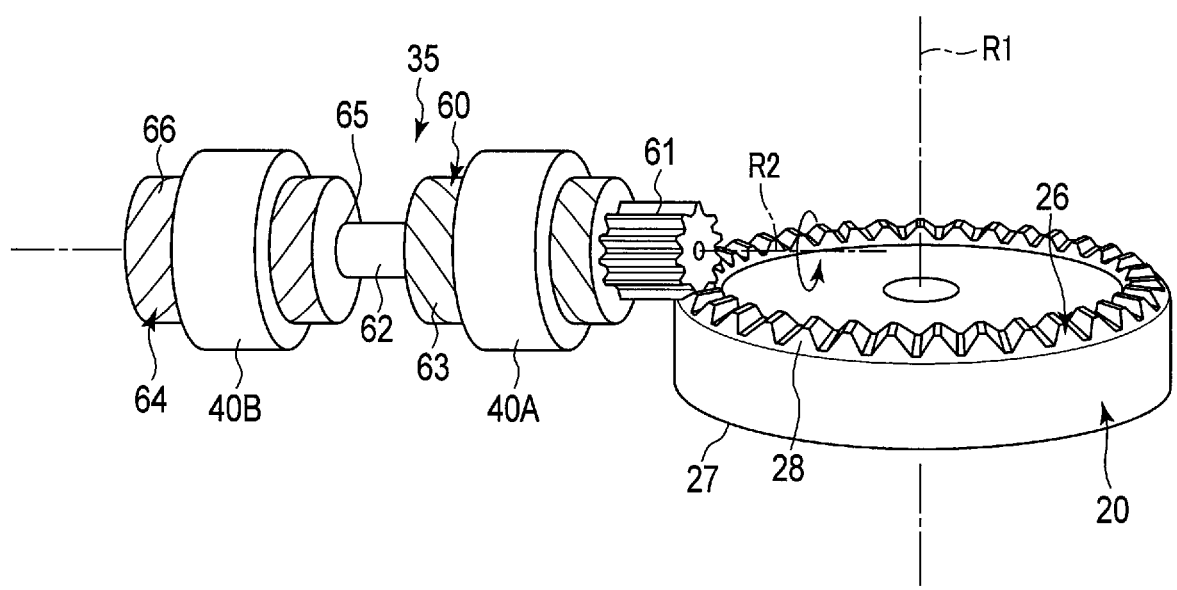
FIG. 12 is a schematic perspective view of the inside of a base member according to an exemplary embodiment.

FIG. 12 is a diagram illustrating the internal configuration of the rotation bases 22 and 30 of another exemplary embodiment. In this embodiment, a crown gear is used for the gear section 28 of the bending operation dial 20, as illustrated in FIG. 12.

In this embodiment, the shaft 35 as a rotor includes a first rotation member 60 and a second rotation member 64. In this embodiment as well, the shaft 35 has the central axis R2 as the rotation axis. The first rotation member 60 includes a gear section 61 on its proximal end, an insertion portion 62 on its distal end, and a left-hand screw portion (first screw portion) 63 between the gear section 61 and the insertion portion 62. The gear section 61 meshes with the gear section 28 of the bending operation dial 20. A spur gear is used for the gear section 61. The gear section 61 has a certain size (fitting length) along the central axis R2. Therefore, the gear section 61 of the shaft 35 and the gear section 28 of the bending operation dial 20 are movable with respect to each other along the central axis R2 while maintaining the state of meshing with each other. The left-hand screw portion 63 (first screw) includes a left-hand thread formed around the central axis R2.

The insertion portion 62 extends along the central axis R2 at the distal end of the first rotation member 60. The cross section of the insertion portion 62 intersecting with (substantially perpendicular to) the central axis R2 has, for example, a D shape, a polygonal shape, or the like.

The second rotation member 64 is attached to the insertion portion 62. The second rotation member 64 includes a connecting hole 65 extending along the central axis R2. The insertion portion 62 is inserted into the connecting hole 65 from the proximal side and is fitted with the connecting hole 65. The cross section of the insertion portion 62 intersecting with (substantially perpendicular to) the central axis R2 has a shape corresponding to that of the insertion portion 62, such as a D shape or a polygonal shape. Thus, the rotation of the second rotation member 64 about the central axis R2 with respect to the first rotation member 60 is restricted. Accordingly, as the first rotation member 60 rotates about the central axis R2 with respect to the rotation base 22, the second rotation member 64 rotates about the central axis R2 together with the first rotation member 60, and the entire shaft 35 rotates about the central axis R2. The second rotation member 64 is movable along the central axis R2 with respect to the first rotation member 60. Namely, the rotation members 60 and 64 are movable along the central axis R2 with respect to each other.

The second rotation member 64 includes a right-hand screw portion (second screw portion) 66. The right-hand screw portion (second screw) 66 includes a right-hand thread formed around the central axis R2. Therefore, the winding direction of the right-hand screw portion 66 is opposite to that of the left-hand screw portion 63, so that the right-hand screw portion 66 includes a thread reversed with respect to the left-hand screw portion 63.

The nut 40A as a first connecting member is screwed to the left-hand screw portion 63 of the shaft 35. Also, the nut 40B as a second connecting member is screwed to the right-hand screw portion 66 of the rotation member 64. In this embodiment, the nuts 40A and 40B are fixed to the rotation base 22, so that the rotation and movement thereof with respect to the rotation base 22 are restricted.

When the shaft 35 rotates about the central axis R2 with respect to the rotation base 22 in response to the operation input performed through the bending operation dial 20, the left-hand screw portion 63 and the right-hand screw portion 66 rotate about the central axis R2 together with the shaft 35. At this time, the left-hand screw portion 63 rotates about the central axis R2 with respect to the nut 40A. As a result, the left-hand screw portion 63 moves along the central axis R2 with respect to the nut 40A and the rotation base 22. Also, the right-hand screw portion 66 rotates about the central axis R2 with respect to the nut 40B. As a result, the right-hand screw portion 66 moves along the central axis R2 with respect to the nut 40B and the rotation base 22. That is, the shaft 35 as a rotor converts the rotational motion about the central axis R2 generated by the operation input performed through the bending operation dial 20 into a rectilinear motion of the left-hand screw portion 63 and the right-hand screw portion 66 along the central axis R2.

The winding directions of the left-hand screw portion 63 and the right-hand screw portion 66 are opposite to each other. Therefore, the operation input performed through the bending operation dial 20 causes the left-hand screw portion 63 (the first rotation member 60) and the right-hand screw portion 66 (the second rotation member 64) to move in directions opposite to each other with respect to the rotation base 22 along the central axis R2.

In this embodiment, the proximal end (one end) of the bending wire 41A is connected to the first rotation member 60. The proximal end (one end) of the bending wire 41B is connected to the second rotation member 64. Therefore, as the rotation members 60 and 64 move in directions opposite to each other along the central axis R2, the bending wires 41A and 41B are driven, so that the end effector 7 is bent.

The end effector 7, the shaft 5, the rotation bases 22 and 30, and the bending operation dial 20 together rotate with respect to the housing 3 about the longitudinal axis C in response to the operation input performed through the rotation operation knob 18. At this time, the driving force (rotational driving force) is also transmitted from the rotation base 22 to the shaft 35 via the nuts 40A and 40B attached to the rotation base 22, so that the shaft 35 and the nuts 40A and 40B rotate with respect to the housing 3 about the longitudinal axis C together with the rotation base 22. Therefore, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

Figure 13:
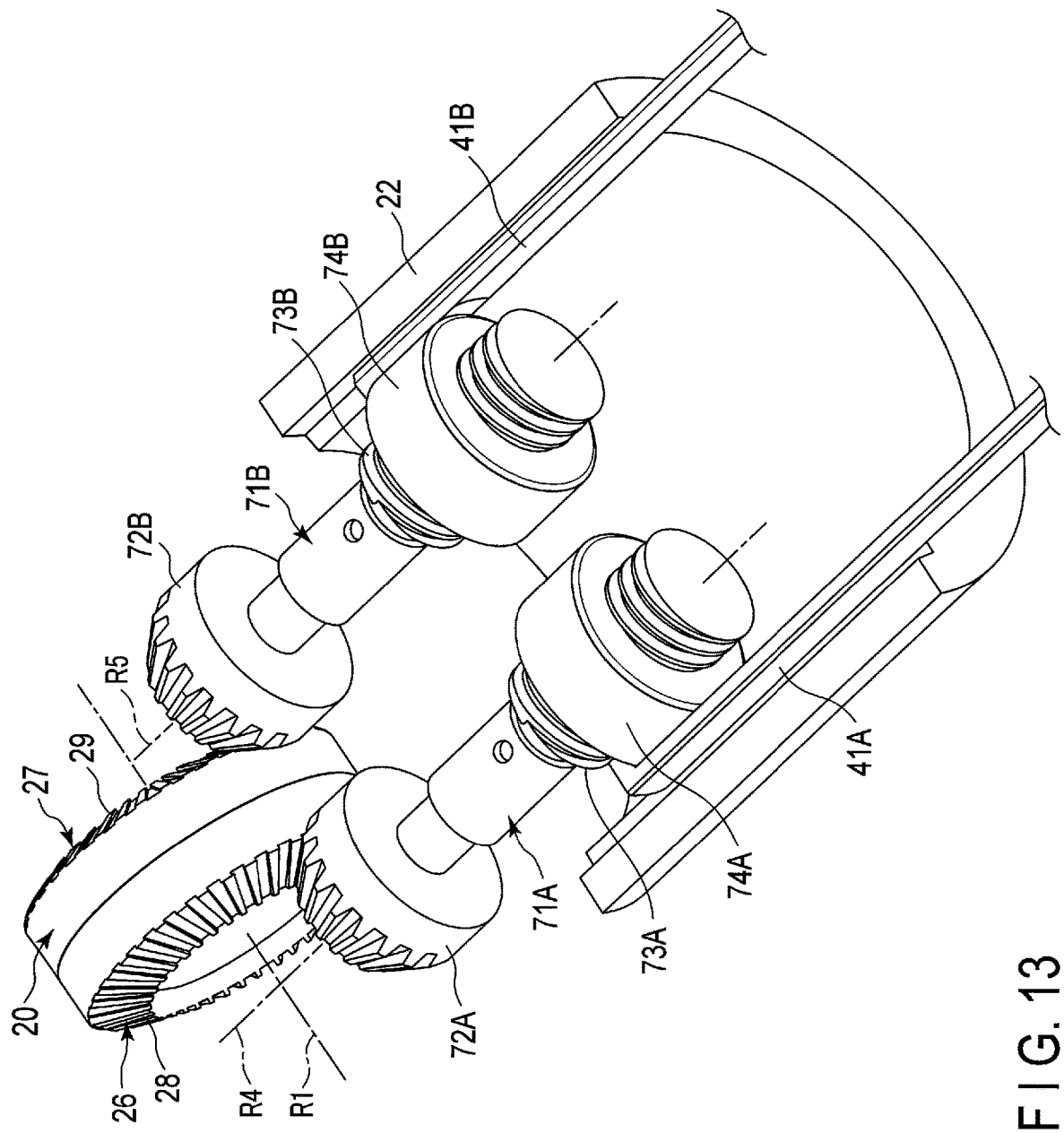
FIG. 13 is a schematic perspective view of the inside of a base member according to an exemplary embodiment.

Next, another exemplary embodiment of the present disclosure will be described with reference to FIG. 13. The same components as those described above with respect to FIGS. 1-12 will be denoted by the same reference symbols, and a description of those components will be omitted. FIG. 13 is a diagram illustrating the internal configuration of the rotation bases 22 and 30 according to the present embodiment. In the present embodiment, a gear section 29 is provided on the second side surface 27 of the bending operation dial 20, as illustrated in FIG. 13. The gear section 29 is formed over the whole circumference of the second side surface 27 around the central axis R1.

A first shaft 71A as a first rotor and a second shaft 71B as a second rotor are mounted inside the rotation base 22. The first shaft 71A extends along the central axis (first rotation axis) R4. The second shaft 71B extends along the central axis (second rotation axis) R5. The central axis R4 and the central axis R5 are substantially parallel to the longitudinal axis C. The movement of the shafts 71A and 71B along the central axes R4 and R5 with respect to the rotation base 22 is restricted. The first shaft 71A is rotatable about the central axis R4 with respect to the rotation base 22, and the second shaft 71B is rotatable about the central axis R5 with respect to the rotation base 22.

A gear section 72A is provided on the proximal end of the first shaft 71A. The gear section 72A contacts the bending operation dial 20 from the first width direction side and meshes with the gear section 28. When the bending operation dial 20 rotates about the central axis R1, a driving force is transmitted to the gear section 72A through the gear section 28, so that the first shaft 71A rotates about the central axis R4 with respect to the rotation base 22.

The first shaft 71A includes a right-hand screw portion (first screw portion) 73A. The right-hand screw portion (first screw) 73A includes a right-hand thread formed around the central axis R4. A nut 74A as a first connecting member (a first connecter) is screwed to the right-hand screw portion 73A. The nut 74A is attached to the rotation base 22. The rotation of the nut 74A about the central axis R4 with respect to the rotation base 22 is restricted. The nut 74A is movable along the central axis R4 with respect to the rotation base 22. Therefore, as the first shaft 71A rotates about the central axis R4 with respect to the rotation base 22, the right-hand screw portion 73A rotates about the central axis R4 with respect to the nut 74A, and the nut 74A moves along the central axis R4 with respect to the shaft 71A and the rotation base 22. The proximal end (one end) of the bending wire 41A as a bending drive member (transmission member) is connected to the nut 74A.

A gear section 72B is provided on the proximal end of the second shaft 71B. The gear section 72B contacts the bending operation dial 20 from the second width direction side and meshes with the gear section 29. When the bending operation dial 20 rotates about the central axis R1, a driving force is transmitted to the gear section 72B through the gear section 29, so that the second shaft 71B rotates about the central axis R5 with respect to the rotation base 22.

The second shaft 71B includes a right-hand screw portion (second screw portion) 73B. The right-hand screw portion (second screw) 73B includes a right-hand thread formed around the central axis R5. Therefore, the winding direction of the right-hand screw portion 73B is the same as that of the right-hand screw portion 73A. A nut 74B as a second connecting member (a second connecter) is screwed to the right-hand screw portion 73B. The nut 74B is attached to the rotation base 22. The rotation of the nut 74B about the central axis R5 with respect to the rotation base 22 is restricted. The nut 74B is movable along the central axis R5 with respect to the rotation base 22. Therefore, as the second shaft 71B rotates about the central axis R5 with respect to the rotation base 22, the right-hand screw portion 73B rotates about the central axis R5 with respect to the nut 74B, and the nut 74B moves along the central axis R5 with respect to the shaft 71B and the rotation base 22. The proximal end (one end) of the bending wire 41B as a bending drive member (transmission member) is connected to the nut 74B.

In the present embodiment as well, the shaft 71A as a rotor converts the rotational motion about the central axis R4 generated by the operation input performed through the bending operation dial 20 into a rectilinear motion of the nut 74A along the central axis R4. Also, the shaft 71B as a rotor converts the rotational motion about the central axis R5 generated by the operation input performed through the bending operation dial 20 into a rectilinear motion of the nut 74B along the central axis R5.

In one embodiment, a bevel gear is used for the gear sections 28, 29, 72A, and 72B. Also, a crown gear may be used for the gear sections 28 and 29, and a spur gear may be used for the gear sections 72A and 72B.

In the present embodiment, when the operation input is performed through the bending operation dial 20, the shaft 71A rotates about the central axis R4 with respect to the rotation base 22, and the shaft 71B rotates opposite to the shaft 71A about the central axis R5 with respect to the rotation base 22. Accordingly, the right-hand screw portion 73A and the right-hand screw portion 73B rotate in directions opposite to each other. Therefore, the nut 74A and the nut 74B move toward the sides opposite to each other in a direction substantially parallel to the longitudinal axis C. As the nut 74A and the nut 74B move toward the sides opposite to each other, the bending wires 41A and 41B are driven, so that the end effector 7 is bent.

The end effector 7, the shaft 5, the rotation bases 22 and 30, and the bending operation dial 20 together rotate with respect to the housing 3 about the longitudinal axis C in response to the operation input performed through the rotation operation knob 18. At this time, the driving force (rotational driving force) is also transmitted from the rotation base 22 to the shafts 71A and 71B and the nuts 74A and 74B attached to the rotation base 22, so that the shafts 71A and 71B and the nuts 74A and 74B rotate with respect to the housing 3 about the longitudinal axis C together with the rotation base 22. Therefore, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

In another exemplary embodiment, the bending wire 41B is connected to the right-hand screw portion 73A of the first shaft (first rotor) 71A, and the bending wire 41A is connected to the right-hand screw portion 73B of the second shaft (second rotor) 71B. In this case, the movement of the nut (first connecting member) 74A along the central axis R4 with respect to the rotation base 22 is restricted, and the movement of the nut (second connecting member) 74B along the central axis R5 with respect to the rotation base 22 is restricted. The shaft 71A is movable along the central axis R4 with respect to the rotation base 22 and the nut 74A, and the shaft 71B is movable along the central axis R5 with respect to the rotation base 22 and the nut 74B. In this embodiment, in response to the operation input for moving the bending operation dial 20 toward one side of the operational direction, for example, the bending wire 41B connected to the shaft 71A moves toward the distal side (to be loosened), and the bending wire 41A connected to the shaft 71B moves toward the proximal side (to be tightened), causing the end effector 7 to bend toward one side of the bending direction (the side indicated by arrow B1 in FIG. 2) with respect to the shaft 5 (the longitudinal axis C). Also, in response to the operation input for moving the bending operation dial 20 toward the other side of the operational direction, the bending wire 41B moves toward the proximal side, and the bending wire 41A moves toward the distal side, causing the end effector 7 to bend toward the other side of the bending direction (the side indicated by arrow B2 in FIG. 2) with respect to the shaft 5 (the longitudinal axis C).

Figure 14:
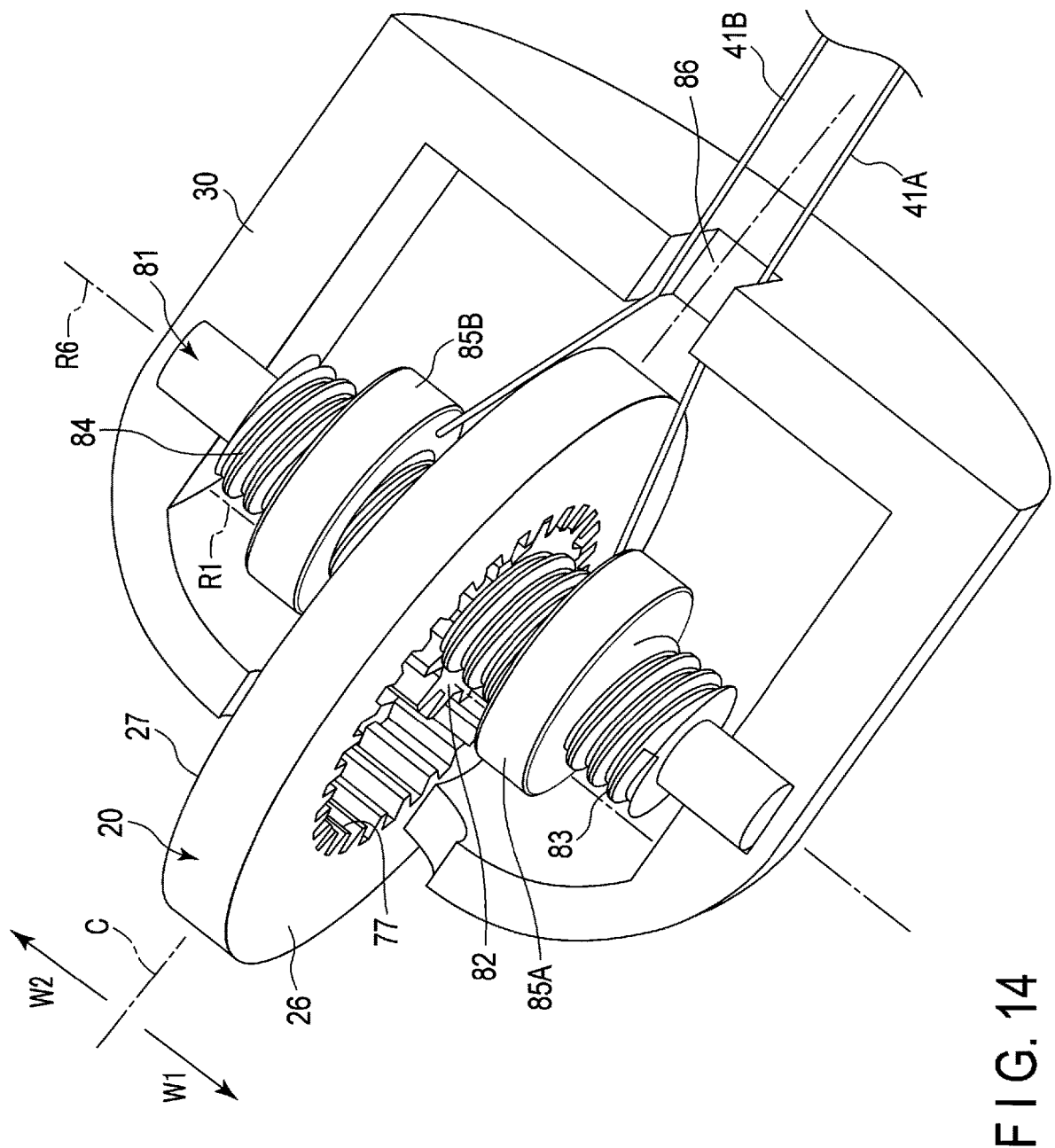
FIG. 14 is a schematic perspective view of the inside of a base member according to an exemplary embodiment.

Next, another exemplary embodiment of the present disclosure will be described with reference to FIG. 14. The same components as those described above with respect to FIGS. 1 to 13 will be denoted by the same reference symbols, and a description of those components will be omitted. FIG. 14 is a diagram illustrating the internal configuration of the rotation base 30 according to the present embodiment. In this embodiment, the bending operation dial 20 includes a gear section 77, which passes through the bending operation dial 20 along the central axis R1 and includes a gear formed on the inner peripheral surface of the gear section 77, as illustrated in FIG. 14. The gear section 77 is formed around the central axis R1.

A shaft 81 as a rotor is inserted through the gear section 77. The shaft 81 extends along the central axis (rotation axis) R6 and is mounted inside the rotation base 30. The central axis R6 is substantially parallel with the central axis R1. That is, the central axis R6 intersects with (is substantially perpendicular to) the longitudinal axis C. The shaft 81 is rotatable about the central axis R6 with respect to the rotation base 30. The movement of the shaft 81 along the central axis R6 with respect to the rotation base 30 is restricted.

The shaft 81 includes a gear section 82. The gear section 82 meshes with the gear section 77 of the bending operation dial 20. For example, a spur gear is used for the gear section 77 and the gear section 82. When the bending operation dial 20 rotates about the central axis R1 in response to the operation input performed through the bending operation dial 20, a driving force is transmitted to the gear section 82 through the gear section 77. Then, the shaft 81 rotates about the central axis R6. In the present embodiment, the longitudinal axis C passes through the gear section 82.

The shaft 81 includes a first left-hand screw portion (first screw portion) 83 and a second left-hand screw portion (second screw portion) 84. The first left-hand screw portion (first screw) 83 and the second left-hand screw portion (second screw) 84 each include a left-hand thread formed around the central axis R6. The winding direction of the second left-hand screw portion 84 is the same as that of the first left-hand screw portion 83. The first left-hand screw portion 83 is positioned on the first width direction side with respect to the gear section 82. The second left-hand screw portion 84 is positioned on the second width direction side with respect to the gear section 82. Therefore, the first left-hand screw portion 83 and the second left-hand screw portion 84 are positioned opposite to each other with respect to the gear section 82. Namely, the first left-hand screw portion 83 and the second left-hand screw portion 84 are positioned opposite to each other with respect to the longitudinal axis C.

A nut 85A as a first connecting member (a first connecter) is screwed to the first left-hand screw portion 83. A nut 85B as a second connecting member (a second connecter) is screwed to the second left-hand screw portion 84. The nuts 85A and 85B are positioned opposite to each other with respect to the gear section 82. The nuts 85A and 85B are attached to the rotation base 30, and the rotation of the nuts 85A and 85B about the central axis R6 with respect to the rotation base 30 is restricted. The nuts 85A and 85B are movable along the central axis R6 with respect to the rotation base 30.

When the shaft 81 rotates about the central axis R6 with respect to the rotation base 30 in response to the operation input performed through the bending operation dial 20, the left-hand screw portions 83 and 84 rotate about the central axis R6 together with the shaft 81. At this time, the left-hand screw portion 83 rotates about the central axis R6 with respect to the nut 85A. As a result, the nut 85A moves along the central axis R6 with respect to the left-hand screw portion 83 and the rotation base 30. Also, the left-hand screw portion 84 rotates about the central axis R6 with respect to the nut 85B. As a result, the nut 85B moves along the central axis R6 with respect to the left-hand screw portion 84 and the rotation base 30.

In the present embodiment as well, the shaft 81 as a rotor converts the rotational motion about the central axis R6 generated by the operation input performed through the bending operation dial 20 into a rectilinear motion of the nuts 85A and 85B along the central axis R6.

The nuts 85A and 85B, at the positions opposite to each other with respect to the longitudinal axis C, move in the same direction, as viewed in the direction substantially perpendicular to the longitudinal axis C (the direction along the central axis R6). Therefore, in the direction substantially perpendicular to the longitudinal axis C (the direction along the central axis R6), one of the nuts 85A and 85B moves away from the longitudinal axis C, and the other of the nuts 85A and 85B approaches the longitudinal axis C.

In the present embodiment, the proximal end (one end) of the bending wire 41A is connected to the nut 85A. The proximal end (one end) of the bending wire 41B is connected to the nut 85B. A guide portion 86 is provided on the distal face of the rotation base 30. The guide portion 86 is a hole that passes through the distal wall of the rotation base 30 from the proximal side to the distal side. The bending wires 41A and 41B are extended from the end effector 7 to the proximal side, and are connected to the nuts 85A and 85B through the guide portion 86. In the present embodiment, the longitudinal axis C passes through the guide portion 86. That is, the guide portion 86 is located between the position where the first left-hand screw portion 83 is provided and the position where the second left-hand screw portion 84 is provided, as viewed along the central axis R6.

When an operation input is performed through the bending operation dial 20, one of the nuts 85A and 85B moves away from the longitudinal axis C, and the other of the nuts 85A and 85B approaches the longitudinal axis C. When one of the nuts 85A and 85B moves away from the longitudinal axis C along the central axis R6, one of the bending wires 41A and 41B moves toward the proximal side with respect to the shaft 5 through the guide portion 86 (to be tightened). When the other of the nuts 85A and 85B approaches the longitudinal axis C along the central axis R6, the other of the bending wires 41A and 41B moves toward the distal side with respect to the shaft 5 through the guide portion 86 (to be loosened). As a result, the bending wires 41A and 41B are driven, so that the end effector 7 is bent.

The end effector 7, the shaft 5, the rotation bases 22 and 30, and the bending operation dial 20 together rotate with respect to the housing 3 about the longitudinal axis C in response to the operation input performed through the rotation operation knob 18. At this time, the driving force (rotational driving force) is also transmitted from the rotation base 30 to the shaft 81 and the nuts 85A and 85B attached to the rotation base 30, so that the shaft 81 and the nuts 85A and 85B rotate with respect to the housing 3 about the longitudinal axis C together with the rotation base 30. Therefore, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

Figure 15:
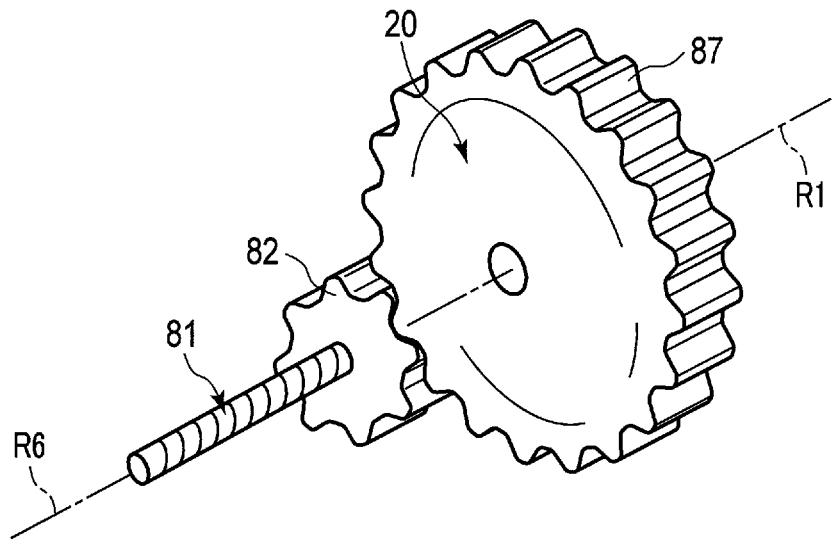
FIG. 15 is a schematic perspective view of the inside of a base member according to an exemplary embodiment.

FIG. 15 is a diagram illustrating the internal configuration of the rotation bases 22 and 30 according to another exemplary embodiment. In this embodiment, a gear section 87 is formed around the central axis R1 on the outer peripheral surface of the bending operation dial 20, as illustrated in FIG. 15. The gear section 87 meshes with the gear section 82 of the shaft 81. For example, a spur gear is used for the gear section 82 and the gear section 87.

When the bending operation dial 20 rotates about the central axis R1 in response to an operation input performed through the bending operation dial 20, a driving force is transmitted to the gear section 87 through the gear section 82, causing the shaft 81 to rotate about the central axis R6.

Figure 16:
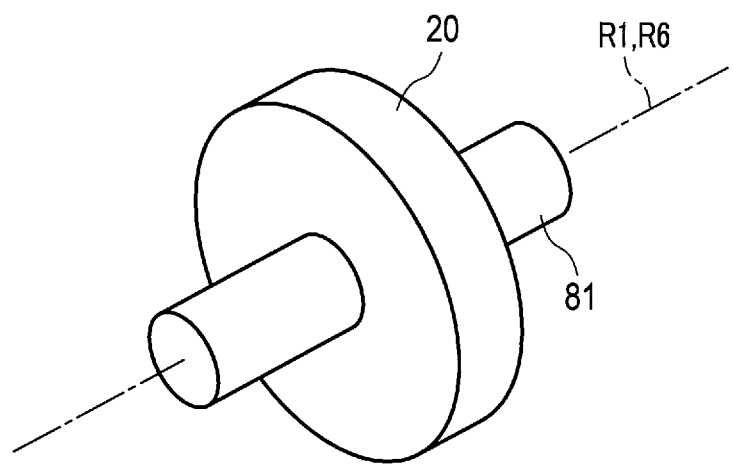
FIG. 16 is a schematic perspective view of the inside of a base member according to an exemplary embodiment.

FIG. 16 is a diagram illustrating the internal configuration of the rotation bases 22 and 30 according to another exemplary embodiment. In this embodiment, the shaft 81 is integrally formed with the bending operation dial 20, as illustrated in FIG. 16. The central axis R6 of the shaft 81 is substantially the same as the central axis R1 of the bending operation dial 20. In this embodiment, the bending operation dial 20 and the shaft 81 rotate integrally about the central axis R1 (central axis R6) in response to the operation input performed through the bending operation dial 20.

FIG. 17 is a diagram illustrating the internal configuration of the rotation bases 22 and 30 according to another exemplary embodiment. In this embodiment, the central axis R6 of the shaft 81 intersects with (is substantially perpendicular to) the longitudinal axis C and extends in a direction intersecting with (substantially perpendicular to) the central axis R1, as illustrated in FIG. 17. As discussed above with respect to FIG. 15, a gear section 88 is formed around the central axis R1 on the outer periphery of the bending operation dial 20. For example, a screw gear is used for the gear section 82 and the gear section 88. The gear section 88 meshes with the gear section 82. When the bending operation dial 20 rotates about the central axis R1 in response to the operation input performed through the bending operation dial 20, a driving force is transmitted to the gear section 82 through the gear section 88. Then, the shaft 81 rotates about the central axis R6.

Figure 18:
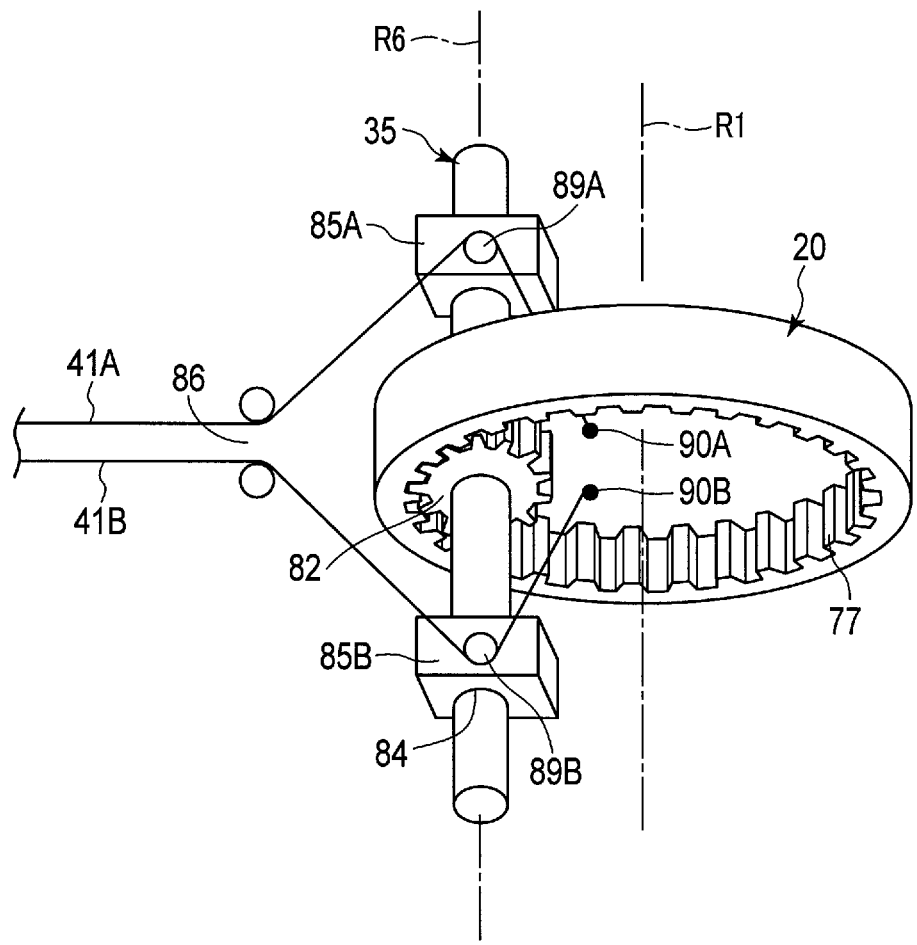
FIG. 18 is a schematic perspective view of the inside of a base member according to an exemplary embodiment.

FIG. 18 is a diagram illustrating the inside of the rotation base 30 according to another exemplary embodiment. As illustrated in FIG. 18, the bending wires 41A and 41B may be connected to the rotation base 30 rather than to the nuts 85A and 85B. In this embodiment, a wire guide 89A is provided to the nut 85A, and a wire guide 89B is provided to the nut 85B. Also, wire fixing portions 90A and 90B are provided to the rotation base 30. The wire fixing portion 90A is positioned closer to the second width direction side than the wire guide 89A. The wire fixing portion 90B is positioned closer to the first width direction side than the wire guide 89B.

The bending wire 41A extends toward the proximal side through the guide portion 86, and bends toward the first width direction side in the guide portion 86. The bending wire 41A is brought into contact with the wire guide 89A from the first width direction side and bends toward the second width direction side. The bending wire 41A is connected to the wire fixing portion 90A. Therefore, the bending wire 41A is pulled toward the first width direction side by the wire guide 89A.

As the wire guide 89A (the nut 85A) moves toward the first width direction side, the bending wire 41A moves toward the proximal side with respect to the shaft 5 (to be tightened). Also, as the wire guide 89A moves toward the second width direction side, the bending wire 41A moves toward the distal side with respect to the shaft 5 (to be loosened).

The bending wire 41B extends toward the proximal side through the guide portion 86, and bends toward the second width direction side in the guide portion 86. The bending wire 41B is brought into contact with the wire guide 89B from the second width direction side and bends toward the first width direction side. The bending wire 41B is connected to the wire fixing portion 90B. The bending wire 41B is pulled toward the second width direction side by the wire guide 89B.

As the wire guide 89B (the nut 85B) moves toward the second width direction side, the bending wire 41B moves toward the proximal side with respect to the shaft 5 (to be tightened). Also, as the wire guide 89B moves toward the first width direction side, the bending wire 41B moves toward the distal side with respect to the shaft 5 (to be loosened).

In this embodiment as well, when an operation input is performed through the bending operation dial 20, one of the nuts 85A and 85B moves away from the gear section 82, and the other of the nuts 85A and 85B approaches the gear section 82. Therefore, one of the bending wires 41A and 41B moves toward the proximal side with respect to the shaft 5 (to be tightened), and the other of the bending wires 41A and 41B moves toward the distal side with respect to the shaft 5 (to be loosened). As a result, the bending wires 41A and 41B are driven, so that the end effector 7 is bent.

In another exemplary embodiment, the bending wire 41B is connected to the left-hand screw portion (first screw portion) 83 of the shaft 81, and the bending wire 41A is connected to the left-hand screw portion (second screw portion) 84 of the shaft 81. In this case, the movement of the nut (first connecting member) 85A and the nut (second connecting member) 85B along the central axis R6 with respect to the rotation base 22 is restricted. The shaft 81 including the left-hand screw portions 83 and 84 is movable along the central axis R6 with respect to the rotation base 22 and the nuts 85A and 85B. In this embodiment, in response to the operation input for moving the bending operation dial 20 toward one side of the operational direction, for example, the bending wire 41B connected to the left-hand screw portion 83 moves toward the distal side (to be loosened), and the bending wire 41A connected to the left-hand screw portion 84 moves toward the proximal side (to be tightened), causing the end effector 7 to bend toward one side of the bending direction (the side indicated by arrow B1 in FIG. 2) with respect to the shaft 5 (the longitudinal axis C). Also, in response to the operation input for moving the bending operation dial 20 toward the other side of the operational direction, the bending wire 41B moves toward the proximal side, and the bending wire 41A moves toward the distal side, causing the end effector 7 to bend toward the other side of the bending direction (the side indicated by arrow B2 in FIG. 2) with respect to the shaft 5 (the longitudinal axis C).

The surgical treatment instrument (1) of the above-described embodiments may include: a holdable housing (3); a shaft (5), which defines a longitudinal axis (C), is extended along the longitudinal axis (C) from the proximal side toward the distal side, and is connected to the distal side of the housing (3); an end effector (7), which is attached to the distal side of the shaft (5) and bends with respect to the shaft (5); a first operation member (18), through which an operation input for rotating the shaft (5) and the end effector (7) about the longitudinal axis (C) with respect to the housing (3) is performed; a second operation member (20), which is attached to the housing (3), and through which an operation input for causing the end effector (7) to bend with respect to the shaft (5) is performed; a rotor (35; 71A, 71B; 81), which is provided inside the housing (3), has a rotation axis (R2; R4, R5; R6), and rotates about the rotation axis (R2; R4, R5; R6) in response to the operation input performed through the second operation member (20); and a transmission member (41A, 41B) connected to the rotor (35; 71A, 71B; 81) and the end effector (7), the transmission member (41A, 41B) transmitting a driving force to the end effector to cause the end effector (7) to bend when the rotor (35; 71A, 71B; 81) rotates about the rotation axis (R2; R4, R5; R6) based on the operation input performed through the second operation member (20). In response to the operation input performed through the first operation member (18), the second operation member (20), the rotor (35; 71A, 71B; 81), and the transmission member (41A, 41B) rotate about the longitudinal axis (C) with respect to the housing (3) together with the shaft (5) and the end effector (7).

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment instrument comprising:
   an elongated member that extends along a longitudinal axis from a proximal side to a distal side;
   a housing, a distal side of which is connected with the elongated member;
   an end effector attached to the distal side of the elongated member, and configured to:
     bend with respect to the elongated member, and
     rotate together with the elongated member about the longitudinal axis with respect to the housing;
   a rotation operator configured to be operated to rotate the elongated member and the end effector about the longitudinal axis with respect to the housing;
   a bending operator attached to the housing, and configured to be operated to bend the end effector with respect to the elongated member;
   a rotor provided inside the housing and configured to rotate about a rotation axis parallel to the longitudinal axis in response to operation of the bending operator;
   a transmitter connected to the rotor and the end effector, and configured to transmit a driving force to the end effector to bend the end effector when the rotor rotates about the rotation axis in response to operation of the bending operator;
   a base disposed inside the housing, the rotor being attached to the base such that movement of the rotor in a direction along the rotation axis is restricted; and
   a connecter which is: (i) attached to the rotor, (ii) connected with the transmitter, and (iii) configured to move in a direction along the rotation axis with respect to the base and the rotor when the rotor rotates about the rotation axis with respect to the base,
   wherein:
     the bending operator, the rotor, the transmitter, and the base are configured to rotate about the longitudinal axis with respect to the housing together with the elongated member and the end effector in response to operation of the rotation operator;
     the transmitter is configured to move in a direction along the longitudinal axis when the connecter moves along the rotation axis with respect to the base and the rotor;
     the rotor comprises:
       a first screw; and
       a second screw having a winding direction opposite to that of the first screw;
     the connecter comprises:
       a first connecter connected with the transmitter and screwed to the first screw; and
       a second connecter connected with the transmitter and screwed to the second screw; and
     the first connecter and the second connecter are configured to move in opposite directions along the rotation axis when the rotor rotates about the rotation axis with respect to the base.

2. The surgical treatment instrument according to claim 1, wherein the instrument is configured to convert rotational motion of the rotor into a rectilinear motion of the transmitter.

3. The surgical treatment instrument according to claim 1, wherein the rotation axis is coaxial with the longitudinal axis.

4. The surgical treatment instrument according to claim 1, wherein regardless of an angular position of the bending operator about the longitudinal axis, an operational direction set by the bending operator is parallel to a bending direction of the end effector with respect to the elongated member.

5. The surgical treatment instrument according to claim 4, wherein the bending operator is configured to be rotatably operated about a central axis with respect to the housing, the central axis intersecting the longitudinal axis, and being parallel to a bending axis of the end effector.

6. The surgical treatment instrument according to claim 1, wherein the bending operator is a dial or a knob.

7. A surgical treatment instrument comprising:
an elongated member that extends along a longitudinal axis from a proximal side to a distal side;
a housing, a distal side of which is connected with the elongated member;
an end effector attached to the distal side of the elongated member, and configured to:
bend with respect to the elongated member, and
rotate together with the elongated member about the longitudinal axis with respect to the housing;
a rotation operator configured to be operated to rotate the elongated member and the end effector about the longitudinal axis with respect to the housing;
a bending operator attached to the housing, and configured to be operated to bend the end effector with respect to the elongated member;
a rotor provided inside the housing and configured to rotate about a rotation axis in response to operation of the bending operator;
a transmitter connected to the rotor and the end effector, and configured to transmit a driving force to the end effector to bend the end effector when the rotor rotates about the rotation axis in response to operation of the bending operator;
a base disposed inside the housing, the base being configured to rotate about the longitudinal axis with respect to the housing together with the elongated member and the bending operator in response to operation of the rotation operator, the rotor being attached to the base such that movement of the rotor in a direction along the rotation axis is restricted; and
a connecter which is: (i) attached to the rotor, (ii) connected with the transmitter, and (iii) configured to move in a direction along the rotation axis with respect to the base and the rotor when the rotor rotates about the rotation axis with respect to the base,
wherein:
the bending operator, the rotor, and the transmitter are configured to rotate about the longitudinal axis with respect to the housing together with the elongated member and the end effector in response to operation of the rotation operator,
the transmitter is configured to move in a direction along the longitudinal axis when the connecter moves in a direction along the rotation axis with respect to the base and the rotor,
the rotor comprises:
a first screw, and
a second screw having a winding direction opposite to that of the first screw,
the connecter comprises:

a first connecter connected with the transmitter and screwed to the first screw, and
a second connecter connected with the transmitter and screwed to the second screw, and
the first connecter and the second connecter are configured to move in opposite directions along the rotation axis when the rotor rotates about the rotation axis with respect to the base.

8. A surgical treatment instrument comprising:
an elongated member that extends along a longitudinal axis from a proximal side to a distal side;
a housing, a distal side of which is connected with the elongated member;
an end effector attached to the distal side of the elongated member, and configured to:
bend with respect to the elongated member, and
rotate together with the elongated member about the longitudinal axis with respect to the housing;
a rotation operator configured to be operated to rotate the elongated member and the end effector about the longitudinal axis with respect to the housing;
a bending operator attached to the housing, and configured to be operated to bend the end effector with respect to the elongated member;
a rotor provided inside the housing and configured to rotate about a rotation axis in response to operation of the bending operator;
a transmitter connected to the rotor and the end effector, and configured to transmit a driving force to the end effector to bend the end effector when the rotor rotates about the rotation axis in response to operation of the bending operator;
a base disposed inside the housing, the base being configured to rotate about the longitudinal axis with respect to the housing together with the elongated member and the bending operator in response to operation of the rotation operator; and
a connecter attached to the base such that movement of the connecter in a direction along the rotation axis is restricted,
wherein:
the bending operator, the rotor, and the transmitter are configured to rotate about the longitudinal axis with respect to the housing together with the elongated member and the end effector in response to operation of the rotation operator;
the rotor is connected with the transmitter, and is configured to rotate about the rotation axis with respect to the base and the connecter to thereby move in a direction along the rotation axis with respect to the base;
the transmitter is configured to move in a direction along the longitudinal axis when the rotor moves in a direction along the rotation axis with respect to the base and the connecter;
the rotation axis is parallel to the longitudinal axis;
the rotor comprises:
a first screw connected with the transmitter; and
a second screw connected with the transmitter, the second screw having a winding direction opposite to that of the first screw;
the connecter comprises:
a first connecter screwed to the first screw; and
a second connecter screwed to the second screw; and
the first screw and the second screw are configured to move in opposite directions along the rotation axis when the rotor rotates about the rotation axis with respect to the base and the connecter.

\* \* \* \* \*